US010900957B2

(12) United States Patent
Hoenes et al.

(10) Patent No.: US 10,900,957 B2
(45) Date of Patent: Jan. 26, 2021

(54) METHOD AND DEVICE FOR GENERATING A CORRECTED VALUE OF AN ANALYTE CONCENTRATION IN A SAMPLE OF A BODY FLUID

(71) Applicant: Roche Diabetes Care, Inc., Indianapolis, IN (US)

(72) Inventors: Joachim Hoenes, Zwingenberg (DE); Christian Ringemann, Mannheim (DE); Andreas Weller, Heidelberg (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 242 days.

(21) Appl. No.: 14/858,617

(22) Filed: Sep. 18, 2015

(65) Prior Publication Data

US 2016/0011178 A1    Jan. 14, 2016

Related U.S. Application Data

(63) Continuation of application No. PCT/EP2014/055418, filed on Mar. 18, 2014.

(30) Foreign Application Priority Data

Mar. 19, 2013    (EP) .................... 13159901

(51) Int. Cl.
| | |
|---|---|
| G01N 33/50 | (2006.01) |
| G01N 33/52 | (2006.01) |
| G01N 33/558 | (2006.01) |
| G01N 21/75 | (2006.01) |
| G01N 27/327 | (2006.01) |
| G01N 33/66 | (2006.01) |

(52) U.S. Cl.
CPC ......... *G01N 33/5094* (2013.01); *G01N 21/75* (2013.01); *G01N 27/3272* (2013.01); *G01N 27/3274* (2013.01); *G01N 33/525* (2013.01); *G01N 33/558* (2013.01); *G01N 33/66* (2013.01)

(58) Field of Classification Search
CPC ........... G01N 27/3272; G01N 27/3271; G01N 27/3274; C12N 11/00
See application file for complete search history.

(56) References Cited

U.S. PATENT DOCUMENTS

| | | | |
|---|---|---|---|
| 5,385,846 A | 1/1995 | Kuhn et al. | |
| 5,604,351 A | 2/1997 | Bisconte | |
| 5,889,585 A | 3/1999 | Markart | |
| 5,962,216 A | 10/1999 | Trouet et al. | |
| 5,997,817 A | 12/1999 | Crismore et al. | |
| 6,055,060 A | 4/2000 | Bolduan et al. | |
| 6,287,451 B1 * | 9/2001 | Winarta | C12Q 1/002 204/403.03 |
| 6,825,918 B2 | 11/2004 | Eisenmann et al. | |
| 7,315,378 B2 | 1/2008 | Phelan et al. | |
| 7,879,624 B2 | 2/2011 | Sharrock | |
| RE42,953 E | 11/2011 | Crismore et al. | |
| 2005/0023152 A1 | 2/2005 | Surridge et al. | |
| 2006/0024835 A1 | 2/2006 | Matzinger et al. | |
| 2006/0240541 A1 | 10/2006 | Petruno et al. | |
| 2007/0015287 A1 | 1/2007 | Robbins et al. | |
| 2007/0048807 A1 | 3/2007 | Song | |
| 2008/0087819 A1 | 4/2008 | Kalveram et al. | |

(Continued)

FOREIGN PATENT DOCUMENTS

| | | |
|---|---|---|
| CN | 1737566 A | 7/2005 |
| CN | 102348808 A | 2/2012 |

(Continued)

OTHER PUBLICATIONS

Arslan et al. "An Amperometric Biosensor for Glucose Determination Prepared from Glucose Oxidase Immobilized in Polyaniline-Polyvinylsulfonate Film" Sensors 2011, 11, 8152-8163.*
J. Hoenes et al.: The Technology Behind Glucose Meters: Test Strips, Diabetes Technology & Therapeutics, vol. 10, Supplement 1, 2008, S-10 to S-26.
Abstract for EP 2636751 A2, downloaded from http://worldwide.espacenet.com on Aug. 23, 2016, 2 pages.
CN Office Action dated May 5, 2016, 11 pages.
English Abstract of EP 0354441, downloaded from http://worldwide.espacenet.com on Jan. 14, 2016, 1 page.
English Abstract of EP 0431456, downloaded from Patent Translate Powered by EPO and Google on Jan. 14, 2016, 2 pages.

(Continued)

*Primary Examiner* — Thane Underdahl
(74) *Attorney, Agent, or Firm* — Woodard, Emhardt, Henry, Reeves & Wagner, LLP

(57) ABSTRACT

Methods for detecting an analyte in a body fluid are described as well as devices and systems adapted for performing such methods. In embodiments of the method, a sample of body fluid is applied to a test element having at least one test field including at least one test material that is adapted to change at least one measurable property in the presence of the analyte. The test element further includes a capillary to guide the sample across said test field in a flow direction. The test element also includes first and second measurement locations offset from each other in the flow direction. The measurable property is measured in at least one first measurement location, providing at least one first measurement value, and it is measured in at least one second measurement location, providing at least one second measurement value. The analyte is detected by using an evaluation algorithm having at least two input variables, wherein at least one first input variable of the at least two input variables includes a difference between the first measurement value and the second measurement value, and at least one second input variable of the at least two input variables includes information relating to an analyte-induced change of the measurable property of the test material in at least part of the test field.

22 Claims, 14 Drawing Sheets

(56) References Cited

U.S. PATENT DOCUMENTS

| | | |
|---|---|---|
| 2009/0304247 A1 | 12/2009 | Petrich et al. |
| 2009/0305332 A1 | 12/2009 | Haendler et al. |
| 2010/0159570 A1 | 6/2010 | Feldman et al. |
| 2011/0201909 A1 | 8/2011 | Emery et al. |

FOREIGN PATENT DOCUMENTS

| | | |
|---|---|---|
| CN | 101598663 A | 12/2019 |
| EP | 0 354 441 | 1/1989 |
| EP | 0 821 234 A2 | 2/1989 |
| EP | 0 431 456 | 11/1990 |
| EP | 0865606 B1 | 9/1998 |
| EP | 0 974 303 A1 | 1/2000 |
| EP | 1 359 409 A2 | 4/2003 |
| EP | 2636751 A2 | 2/2012 |
| JP | 2003-156469 A | 5/2003 |
| JP | 2005-523443 A | 8/2005 |
| JP | 2005/303 968 | 10/2005 |
| JP | 2007303968 A | 11/2007 |
| JP | 2010-002219 A | 1/2010 |
| JP | 2011-158483 A | 8/2011 |
| KR | 10-2006-0049942 | 8/2008 |
| WO | WO 1997/021090 | 6/1997 |
| WO | WO 1997/036168 A1 | 10/1997 |
| WO | WO 2000/73785 A2 | 7/2000 |
| WO | WO 2003/089858 | 10/2003 |
| WO | WO 2006/138266 A2 | 12/2006 |
| WO | WO 2007/012494 A1 | 2/2007 |
| WO | WO 2008/150438 A1 | 11/2008 |
| WO | WO 2009/103540 A1 | 8/2009 |
| WO | WO 2010/122990 A1 | 10/2010 |
| WO | WO 2011/012269 A2 | 2/2011 |
| WO | WO 2011/012270 | 2/2011 |
| WO | WO 2011/012271 A2 | 2/2011 |
| WO | WO 2012/091728 A1 | 7/2012 |

OTHER PUBLICATIONS

English Abstract of EP 0821234 A2, downloaded from http://worldwide.espacenet.com on Jan. 14, 2016, 1 page.
English Abstract of EP 0974303 A1, downloaded from http://worldwide.espacenet.com on Jan. 14, 2016, 1 page.
English Abstract of JP 2005/303968, downloaded from http://worldwide.espacenet.com on Jan. 14, 2016, 2 pages.
English Abstract of JP 2007/303968 A, downloaded from http://worldwide.espacenet.com on Jan. 14, 2016, 2 pages.
English Abstract of KR 10-2008-0049942, dated Jun. 5, 2008, printed from http://engpat.kipris.or on Jul. 28, 2017, 2 pages.
Translation of CN Office Action dated May 5, 2016, 15 pages.
WO 03/089658 A1 (EESR dated Jul. 26, 2013) plus International Search Report dated Apr. 14, 2014, 35 pages.
WO 2000/73785 A2 (EESR dated Jul. 26, 2013) plus Inernational Search Report dated Apr. 14, 2014, 40 pages.
WO 2008/150436 A1 (EESR dated Jul. 26, 2013) plus Inernational Search Report dated Apr. 4, 2014, 24 pages.
WO 2012/091728 A1 (EESR dated Jul. 26, 2013) plus Inernational Search Report dated Apr. 14, 2014, 91 pages.

* cited by examiner

METHOD AND DEVICE FOR GENERATING A CORRECTED VALUE OF AN ANALYTE CONCENTRATION IN A SAMPLE OF A BODY FLUID

CLAIM OF PRIORITY

The present application is a continuation of International Patent Application No. PCT/EP2014/055418, filed Mar. 18, 2014, which is based on and claims priority to European Patent Application No. 13159901.1, filed Mar. 19, 2013. Each patent application is incorporated herein by reference as if set forth in its entirety.

TECHNICAL FIELD OF THE INVENTION

The present application relates to a method and device for detecting an analyte in a body fluid, and more particularly to generating a corrected value of the analyte using measurement values measured in different locations of a test field of a test element to which the body fluid is applied.

BACKGROUND

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of test elements comprising one or more test chemistries, which, in presence of the analyte to be detected, are capable of performing one or more detectable detection reactions, such as optically detectable detection reactions. With regard to these test chemistries, reference may be made e.g. to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing the present invention.

Typically, one or more optically detectable changes in the test chemistry are monitored, in order to derive the concentration of the at least one analyte to be detected from these changes. Examples of test fields, test chemistries and methods for monitoring one or more optically detectable changes in the test fields are disclosed in EP 0 821 234 A2. Thus, as an example, the relative remission of the test field may be optically detected as a function of time, up to a defined end point of the chemical detection reaction. From the change in relative remission, the concentration of the analyte may be derived. Similar measurements detecting the quantity of light reflected from the test field as a function of time, up to a defined end point of the detection reaction, are disclosed in EP 0 974 303 A1.

For detecting the at least one change of optical properties of the test field, various types of detectors are known in the art. Thus, various types of light sources for illuminating the test fields as well as various types of detectors are known. Besides single detectors such as photodiodes, various types of devices using detector arrays having a plurality of photosensitive devices are known, providing an arrangement for measuring the concentration of an analyte contained in a sample of a body fluid. In one known arrangement, a light source and a detector array may be provided. Similarly, a known apparatus for determining the concentration of an analyte in a physiological sample may include at least one light source and a detector array. See, e.g., US 2011/0201909 A1 and EP 1 359 409 A2 and WO 2006/138226 A2.

Further, when using detector arrays, methods are known in the art for detecting errors and artifacts in the images acquired by the detector arrays. One such method includes a correction algorithm which, inter alia, is capable of correcting for imperfections present in the reaction spot observed by the detector array. Another method includes means for determining whether a sufficient amount of sample is present on each of a plurality of different detector areas, wherein only light detected from those areas determined to have sufficient sample is used for determining the concentration of the analyte. In yet another method an arrangement and an algorithm for calculating the concentration of an analyte contained in a sample include detecting a color change rate of a test chemical, and deriving a hematocrit value from the color change rate. An appropriate correction factor indicative of the hematocrit can then be used for correcting a glucose concentration.

It has been known that measurement of a soluble analyte in a suspension additionally comprising at least one particulate compound is hampered by the fact that the measured value may deviate from the actual concentration depending on the concentration of said particulate compound. For the example of determining blood glucose levels, it has been proposed to use viscosity of the sample as a surrogate measure of the concentration of blood cells, i.e. the hematocrit. See, e.g., JP 2005/303 968. However, the viscosity of a blood sample depends on several other parameters, such as the concentration of fibrinogen and globulins, red blood cell and platelet aggregation, and the like, so the correction derived from direct or indirect viscosity measurement generally is affected by these parameters, thus rendering such a correction inaccurate to a certain extent. For example, it is known to use a biosensor using single-point measurement of the resistance between two electrodes to estimate the hematocrit level in the sample and to correct the measured value based on the estimated hematocrit level and on a set of pre-determined, empirical constants. See, e.g., WO 2003/089658.

There is, thus, a need in the art to provide reliable means and methods to determine the concentration of a soluble analyte in a suspension further comprising a particulate compound and to provide for a correction of the measured concentration in dependence of the concentration of the particulate compound.

SUMMARY

This object and others that will be appreciated by a person of ordinary skill in the art have been achieved according to the embodiments of the present invention disclosed herein. In one embodiment, the present invention comprises a method for detecting an analyte in a body fluid, the method having the following steps:

a) applying a sample of the body fluid to a test element, said test element comprising at least (i) a test field comprising at least one test material adapted to change at least one measurable property in the presence of the analyte, (ii) a capillary element adapted to guide the sample across said test field in a flow direction, (iii) a first and a second measurement location within said test field, wherein the second measurement location is offset from the first measurement location in the flow direction; and b) measuring the measurable property in said at least one first measurement location, thereby generating at least one first measurement value; and c) measuring the measurable property in said at least one second measurement location, thereby generating at least one second measurement value; and d) detecting the analyte by using an evaluation algorithm having at least two input variables, wherein (i) at least one first input variable of the at least two input variables includes an information on a difference between the first measurement value and the second measurement value, and (ii) at least one second input variable of the at least two input variables includes a measurement information on an analyte-induced change of the measurable property of the test material in at least part of the test field.

In a further embodiment, the present invention relates to a test device and to a test system adapted for performing the method of the present invention, and to the use of a difference of at least two measurement values measured in at least two different locations of a test field of a test element for generating a corrected value of an analyte concentration in a sample of a body fluid.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
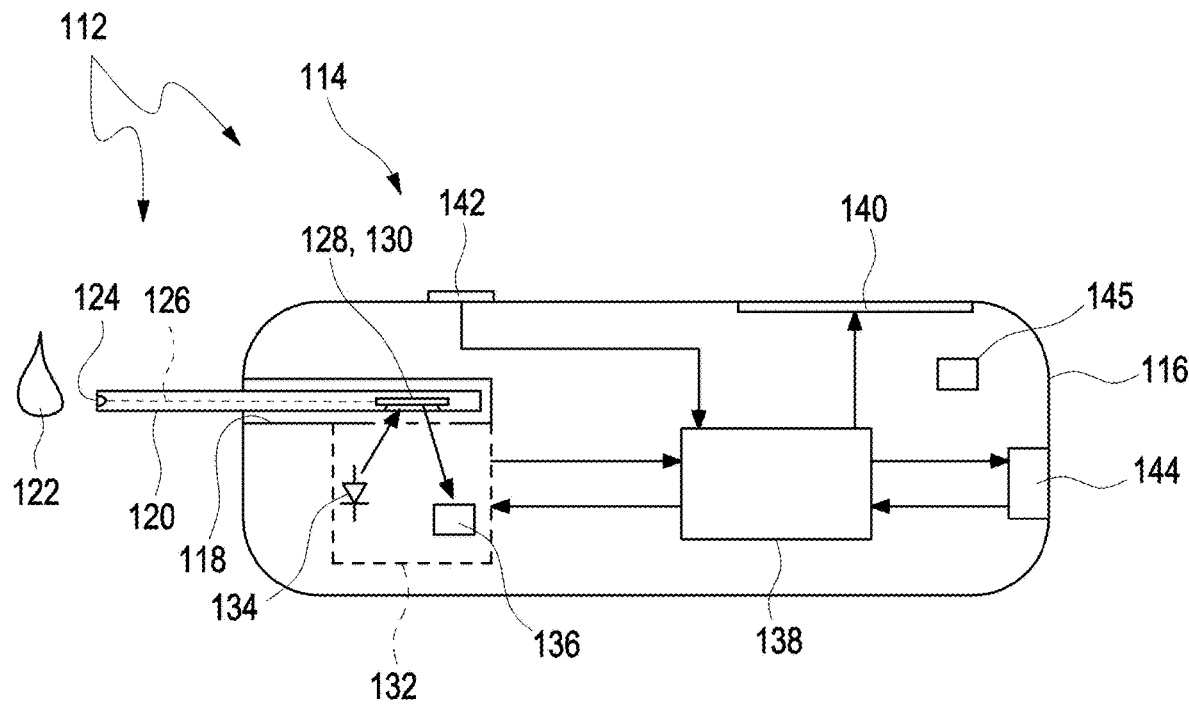
FIG. 1 shows a cross-sectional view of an exemplary embodiment of a test system and a test device according to the present invention.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

As used herein, the expressions "have", "comprise" and "contain" as well as grammatical variations thereof are used in a non-exclusive way. Thus, the expression "A has B" as well as the expression "A comprises B" or "A contains B" may both refer to the fact that, besides B, A contains one or more further components and/or constituents, and to the case in which, besides B, no other components, constituents or elements are present in A.

The method of the present invention, typically is an in vitro method. Moreover, it may comprise steps in addition to those explicitly mentioned above. For example, further steps may relate, e.g., to obtaining a sample of a body fluid for step a), or displaying the result of the determination on an output element in step d). Moreover, one or more of said steps may be performed by automated equipment.

The term "analyte", as used herein, relates to a chemical compound present in a body fluid. In some instances, the analyte is a small molecule, i.e., the analyte is not a biological macromolecule; for example, the analyte may be an organic molecule, including an organic molecule capable of undergoing a redox reaction in the presence of the test chemistry according to the present invention. In some instances, the analyte is a molecule of the subject's metabolism. An analyte may also be a low molecular weight chemical compound, such as a chemical compound with a molecular mass of less than 1000 u (1000 Da; 1.66×10-24 kg). In some of the described embodiments, the analyte is selected from the list consisting of glucose, lactate, cholesterol, and triglycerides. In one particular embodiment, the analyte is blood glucose and the actual concentration to be determined is at least 10 mg/dL, at least 50 mg/dL, at least 60 mg/dL, at least 70 mg/dL, at least 80 mg/dL, at least 90 mg/dL, at least 100 mg/dL, at least 110 mg/dL, at least 120 mg/dL, at least 130 mg/dL, at least 140 mg/dL, or at least 150 mg/dL.

As used herein, the term "body fluid" relates to all bodily fluids of a subject known to comprise or suspected to comprise the analyte of the present invention, including blood, plasma, lacrimal fluid, urine, lymph, cerebrospinal fluid, bile, stool, sweat, and saliva. In some instances, the body fluid comprises at least one particulate component; the size difference between the particulate component and the analyte allows the separation of the particulate component from the analyte by a separation layer. In other instances, the size ratio (average size of the particulate component versus size of the analyte) is at least 10, at least 20, at least 50, at least 100, at least 200, at least 500, at least 1000, at least 2000, at least 5000, or at least 10000, at least 100000, or at least 1000000. In more specific instances, the particulate compound is cells; such as blood cells, in which instance the body fluid is blood, and the concentration of a particulate compound is the volume percentage of blood cells therein, i.e. the hematocrit. The term "sample" is understood by the skilled person and relates to any subportion of a bodily fluid, removed from the subject prior to applying said sample to a test element. Samples can be obtained by well-known techniques including, e.g., venous or arterial puncture, epidermal puncture, and the like.

The term "detecting" relates to the quantification of the amount of analyte present in a sample of a body fluid, i.e. measuring the amount or concentration of said analyte semi-quantitatively or quantitatively. The detection of the amount of the analyte can be accomplished in a variety of ways known to the skilled person or detailed herein below. In accordance with the present invention, detecting the amount of the analyte can be achieved by all known means for detecting the amount of said analyte in a sample, provided that they are adapted to specifically detect the analyte of the present invention and are compatible with the requirements of the present invention. The term "amount" as used herein encompasses the absolute amount of the analyte referred to herein, the relative amount or concentration of the analyte referred to herein as well as any value or parameter which correlates thereto. Such values or parameters comprise intensity signal values from all specific physical or chemical properties obtained from the analyte referred to herein by measurements. It is to be understood that values correlating to the aforementioned amounts or parameters can also be obtained by all standard mathematical operations.

The term "test element", as used herein, relates to a unit comprising the elements as described herein below i.e., the test element comprises at least one capillary element and at least one test field. In one aspect, the test element is selected from an optical test element and an electrochemical test element. The test element may further optionally comprise at least one puncture element, such as at least one lancing element, which may be mounted movably with regard to the test field, in order to perform a puncture motion, a sampling motion or a lancing motion, thereby generating an incision in a skin surface. Typically, the test field remains in a fixed position during the puncture, sampling or lancing motion, wherein a sample of a body fluid is transferred onto the test field, such as by a capillary action and/or by pressing the puncture element or a part thereof onto the test field after the puncture, sampling or lancing motion. In various embodiments, the test element is a test strip, a test tape, or a test disc.

As used herein, the term "capillary element" relates to any type of element adapted for taking up and/or transporting a liquid by capillary action. The capillary element may comprise a closed channel, such as a channel in a hollow needle, and/or an open channel, such as a capillary groove or a capillary slit. The closed channel may circumferentially be enclosed by a tubular capillary wall, whereas the open channel may provide an open surface along a longitudinal axis of the channel. In all embodiments, however, at least a part of the circumference of the capillary element is formed by or comprises at least part of the test field and the capillary element is adapted to guide a sample across the test field in a flow direction. In various embodiments, the capillary extends in longitudinal direction over at least 0.5 mm, 0.75 mm, 1 mm, 1.25 mm, 1.5 mm, 1.75 mm, 2 mm, 2.5 mm, 3 mm, 3.5 mm, 4 mm, 4.5 mm, 5 mm, or 10 mm. Generally, the capillary element comprises at least one capillary slit extending across at least a part of the test field. In some instances, the capillary slit is formed by a surface of the test field and a guide surface disposed at a distance above the surface of the test field. In other instances, said guide surface is formed by a surface of a cover plate being disposed above the surface of the test field. A capillary slit may have a width of 30 µm to 300 µm, and in various embodiments the capillary slit has a width of 40 µm to 200 µm, of 50 µm to 100 µm, of 60 µm to 80 µm, or of 70 µm. In some instances, the test field is applied to a substrate on a surface of the substrate facing the capillary element. In some embodiments, said substrate contains at least one detection window wherein the measurable property is measured through the detection window. In such embodiments, the detection window comprises an opening or a transparent detection window.

The term "test field" relates to a continuous or discontinuous amount of test chemistry, which may be held by at least one carrier, such as by at least one carrier film. Thus, the test chemistry may form or may be comprised in one or more films or layers of the test field, and/or the test field may comprise a layer setup having one or more layers, wherein at least one of the layers comprises the test chemistry. Thus, the test field may comprise a layer setup disposed on a carrier, wherein the sample of the body fluid may be applied to the layer setup from at least one application side, such as from an edge of the test field and/or from an application surface of the test field. The test field may have a multilayer setup, the multilayer setup comprising at least one detection layer having the at least one test material and further comprising at least one separation layer adapted for separating off at least one particulate component contained in the body fluid, wherein the separation layer is located between the detection layer and the capillary element. It is understood by the skilled person that all layers present optionally between the body fluid and the test field are selected as to allow passage of at least the analyte. In various embodiments, the volume enclosed between the test layer and the separation layer is at most 1%, at most 2%, at most 3%, at most 4%, at most 5%, at most 6%, at most 7%, at most 8%, at most 9%, at most 10%, at most 15%, at most 20%, at most 25%, at most 30%, at most 35%, at most 40%, at most 45%, at most 50%, at most 75%, or at most 95% of the volume encompassed by the capillary element.

The terms "test chemistry" or "test material" refer to a substance or mixture of substances which is adapted to change at least one measurable property in the presence of the analyte. The test material may perform at least one optically or electrochemically detectable detection reaction in the presence of the analyte. Further, the detection reaction may be a redox reaction. Even further, the detection reaction may produce redox equivalents and/or electrons as intermediates and/or products. The test reaction may be at least in part mediated by at least one enzyme, in which case the test material comprises at least one enzyme adapted for performing at least one enzymatic reaction in the presence of the analyte. The detection reaction may imply a color change of the test chemistry or of at least one part thereof. With regard to the test chemistry, various possibilities of designing the test chemistry are known in the art. In this regard, reference may be made to the above-mentioned prior art documents. Specifically, reference may be made to J. Hoenes et al.: The Technology Behind Glucose Meters: Test Strips, Diabetes Technology & Therapeutics, Volume 10, Supplement 1, 2008, S-10 to S-26, incorporated by reference herein in its entirety. However, other types of test chemistry are possible. The test chemistry may comprise at least one enzyme which may directly or indirectly react with the analyte, such as with a high specificity, wherein, further, one or more optical indicator substances are present in the test chemistry, which perform at least one optically detectable property change when the at least one enzyme reacts with the analyte. Thus, the at least one indicator may comprise one or more dyes performing a color changing reaction indicative of the enzymatic reaction of the at least one enzyme and the analyte. Thus, the at least one enzyme may comprise glucose oxidase and/or glucose dehydrogenase. However, other types of enzymes and/or other types of test chemistry or active components of the test chemistry may be used.

Thus, it is also envisaged by the present invention that the test chemistry includes a chemical reagent for reacting with the analyte to produce an electrochemical signal that represents the presence of the analyte in the sample fluid. The test chemistry is selected in respect to the analyte to be assessed. As is well known in the art, there are numerous chemistries available for use with each of various analytes. The selection of an appropriate chemistry is therefore well known within the skill in the art, and further description herein is not required in order to enable one to make and use the present invention.

In the case of glucose as an analyte, the active components of the test chemistry will typically include an enzyme utilizing glucose and a redox mediator. Such enzyme comprises at least one of glucose oxidase and glucose dehydrogenase. The enzyme oxidizes glucose in the sample, and the mediator in turn reacts with the reduced enzyme. The mediator thereafter shuttles the redox equivalent of analyte product to the electrode surface by diffusion. There the mediator is oxidized quantitatively at a defined anodic potential and the resulting current is related to the apparent glucose concentration. There are a number of reagent systems suitable for the detection of glucose, and examples comprise AC Excitation, Analyte Sensors, and Biosensor applications, U.S. Pat. Nos. 5,385,846 and 5,997,817, and U.S. (Reissue) patent application Ser. No. 10/008,788 ("Electrochemical Biosensor Test Strip"), "),"); the cNAD chemistry as described in WO 2007/012494, WO 2009/103540, WO 2011/012269, WO 2011/012270, and WO 2011/012271; and the SCV chemistry as described in EP 0 354 441, EP 0 431 456, which are hereby incorporated by reference in their respective entireties. The glucose chemistry utilizes the redox mediator to mediate a current between the working electrode and the glucose analyte, which otherwise is not well suited for direct electrochemical reaction on an electrode. The mediator functions as an electron transfer agent that shuttles electrons between the analyte and the electrode. A great number of redox species are known and can be used as the redox mediator. In general, the redox mediators are rapidly reducible and oxidizable molecules. Examples include ferricyanide, nitrosoaniline and derivatives thereof, and ferrocene and its derivatives.

It follows from the above, that the at least one measurable property may be any property of the test chemistry which changes in the presence of the analyte and which can be transferred into a physical signal of any kind. The change of the measurable property and/or the signal generatable therefrom are proportional to the concentration of the analyte in the sample. As described above, in some embodiments the measurable property is a change in color and/or in color intensity of the test chemistry, i.e., a change in the absorption and/or emission spectrum of the test chemistry. Thus, in the change of the measurable property the optical property may be selected from the group consisting of: a reflection property, such as reflectance and/or remission; transmission property, such as absorption; a color; a luminescence, such as fluorescence. Also, the measurable property may be the concentration of a reduced or an oxidized redox mediator as described above; e.g., the measurable property may be the redox state of said mediator comprised in the test chemistry.

Methods of converting the measurable property as defined above into a physical signal which can be read as a measurement value are well known in the art and are described e.g., in EP 0 821 234, EP 0 974 303, and US 2005/0023152.

The term "measurement location", as used herein, relates to an area within the test field. In various embodiments, the location extends over at most 1%, at most 5%, at most 10%, at most 20%, at most 30%, at most 35%, at most 50%, or at most 75% of the length of the test field, the term "length of a test field", as used in this specification, relating to the dimension of the test field in the flow direction of the capillary element. Thus, in a test field having a length of 2-2.5 mm, the location extends over at most 0.05 mm, at most 0.1 mm, at most 0.15 mm, at most 0.2 mm, at most 0.25, at most 0.3 mm, at most 0.5 mm, at most 1 mm, at most 1.5 mm, at most 2 mm, or at most 5 mm in the flow direction. Also, the location may extend over at most 5%, at most 10%, at most 20%, at most 30%, at most 35%, at most 40%, at most 45%, at most 50%, at most 55%, at most 65%, at most 70%, at most 80%, at most 90%, or at most 100% of the width of the test field. It is understood by the skilled person that the geometry, i.e. the shape, of the location may vary, depending on the detection system used.

The terms "first measurement location" or "first location", as used herein, relate to a first area within the test field. In various embodiments, the first location may be centered within the first 75%, within the first half, within the first third, within the first quarter, within the first fifth, within the first sixth, within the first seventh, within the first eighth, within the first ninth, within the first tenth, or within the first percent of the length of the test field, as determined starting from the application site of the sample. It is understood by the skilled person that a minimum distance from said application site may be necessary to obtain appropriate detection conditions.

Mutatis mutandis, the terms "second measurement location" or "second location" relate to a second area within the test field, wherein the second location is offset from the first location in the flow direction. In various embodiments, the second location may be centered at an offset from the first location in the flow direction by at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the length of the test field.

It is understood by the skilled person that the parameters detailed above can be combined independently, e.g. in a test field of approx. 2 mm (longitudinal=flow direction)×1.75 mm (width), the first location may be centered at 0.2 mm (10%), extend in the flow direction over 0.3 mm (15%), and have a width of 0.35 mm (20%) and the second location may be centered at 1 mm (40% offset from the first location), extend in the flow direction over 0.2 mm (10%) and have a width of 0.7 mm (40%). However, the length and width of the first and the second location and their geometry may be substantially the same for a given test field.

The term "measurement value", as used herein, relates to a value of a physical signal generated by the test chemistry and determined as detailed above and correlating to the concentration of an analyte in a sample. In one embodiment, the measurement value is the value considered to most reliably correlate to the concentration of an analyte in a sample. It is understood that obtaining a measurement value may comprise several measurements of a measurable property over time and selecting the measurement value according to the data thus obtained, as detailed, e.g. in EP 0 974 303. In various embodiments, the second measurement value is obtained before the first measurement value or the second measurement value is measured within less than 5 s, less than 1 s, less than 0.9 s, less than 0.8 s, less than 0.7 s, less than 0.6 s, less than 0.5 s, less than 0.4 s, less than 0.3 s, less than 0.2 s, less than 0.1 s, or less than 0.01 s after the first measurement value. In other embodiments, the first and the second measurement value are measured essentially simultaneously, or even measured simultaneously, e.g., a predetermined time span after application of the sample of the body fluid to the test element. In yet other embodiments, the first and the second measurement value are measured at a point in time at which a measurement curve indicating the measurable property as a function of time fulfills at least one predetermined condition, such as at least one threshold condition wherein a slope of the measurement curve is below or above a predetermined threshold. In one embodiment, the first measurement value is measured at a point in time at which a measurement curve indicating the measurable property at the first measurement location as a function of time fulfills at least one predetermined condition, such as at least one threshold condition wherein a slope of the measurement curve is below or above a predetermined threshold, and the second measurement value is measured at a point in time at which a measurement curve indicating the measurable property at a second measurement location as a function of time fulfills at least one predetermined condition, such as at least one threshold condition wherein a slope of the measurement curve is below or above a predetermined threshold. The first and the second measurement value may be measured simultaneously at a point in time at which a measurement curve indicating the measurable property at the first measurement location or at the second measurement location as a function of time fulfills at least one predetermined condition such as at least one threshold condition wherein a slope of the measurement curve is below or above a predetermined threshold. The first measurement value and the second measurement value may be selected from the group consisting of: an optical measurement value, such as remission; an electrical measurement value, such as current and/or a voltage. Generating at least one of the first and the second measurement value may imply using at least one detector for generating the measurement value. Said detector may include at least one light source for illuminating at least one of the first location and the second location and at least one optically sensitive element adapted to determine detection light from at least one of the first location and the second location. The at least one first location and the at least one second location may be illuminated by one of: light having the same wavelengths, light having different wavelengths. Thus, in one embodiment, the detector comprises at least two separate light sources, e.g., light emitting diodes (LEDs), having the same wavelengths: a first light source illuminating a first location and a second light source illuminating a second location. In one such case, illumination of said first location by said first light source is shifted in time as specified above relative to illumination of said second location by said second light source. In other cases, the detector comprises at least two separate light sources, e.g., light emitting diodes (LEDs), having different modulation frequencies: a first light source illuminating a first location with a first modulation frequency and a second light source illuminating a second location with a second modulation frequency. In such case, illumination of said first location by said first light source is shifted in time as specified above relative to illumination of said second location by said second light source; in alternative cases, illumination of said first location by said first light source is not shifted in time relative to illumination of said second location by said second light source. It is understood by the skilled artisan that the above applies mutatis mutandis in case more than two light sources and/or more than two measurement locations are used.

The detection light may be selected from the group consisting of: light reflected by the test field in at least one of the first location and the second location, light transmitted by the test field in at least one of the first location and the second location, light emitted by the test field in at least one of the first location and the second location.

The optically sensitive element may comprise at least one element adapted to detect light emitted by a light source and reflected and/or transmitted by a test field. Said optically sensitive element may, e.g., be a photo diode. It is understood by the skilled person that in case the illumination of a first location by a first light source is shifted in time relative to illumination of a second location by a second light source as specified above, the detection lights may be detected by one, i.e. by the same, optically sensitive element. The skilled person also understands that in case a first location is illuminated by a first light source having a different modulation frequency as compared to a second light source illuminating a second location, the detection lights may also be detected by one, i.e. by the same, optically sensitive element. In other embodiments, the optically sensitive element comprises at least one one-dimensional or two-dimensional matrix of optically sensitive elements, such as at least one camera chip, including at least one CCD chip. It is understood by the skilled artisan that in case at least one one-dimensional or two-dimensional matrix of optically sensitive elements comprising at least two optically sensitive elements arranged in flow direction is used, it is possible to define a measurement location according to the present invention by selecting at least two different optically sensitive elements located at different positions along the flow direction and by detecting the signals generated by said at least two different optically sensitive elements. Thus, the sensor may comprise at least one one-dimensional or two-dimensional matrix of optically sensitive elements comprising at least two optically sensitive elements arranged in flow direction.

From the above, it is understood that the terms "first" and "second" are solely used in order to enable differentiation between two terms and, in the case of the term "measurement location", do only have a temporal implication in as far as the first location is wetted by the sample before the second location, as detailed above. However, the measuring of the measurable property at the first and at the second location is performed at a point in time where both locations have been wetted by the sample.

As used herein, the term "first input variable" relates to an input variable comprising an information on the difference between the first measurement value and the second measurement value. It is understood that the first variable may result from any mathematical operation providing or conserving said information. The first variable may be the difference of the first and the second measurement value, or the difference of the second and the first measurement value. It is, however, understood by the skilled person that said information is also comprised in the value pair first and second measurement value itself. The first input variable may include an information on a gradient of measurement values over at least part of the test field, wherein the gradient of measurement values over at least part of the test field may be a gradient in the flow direction.

The term "second input variable" relates to an input variable including a measurement information on an analyte-induced change of the test material in at least part of the test field. The value of the second variable may be obtained from any location within the test field. It is understood that said location may be different from both the first and the second location, i.e. be a third location. The definitions above may apply to the third location as well, as a whole or in part. Thus, e.g., the third location is centered within the first 99%, the first 75%, within the first half, within the first third, within the first quarter, within the first fifth, within the first sixth, within the first seventh, within the first eighth, within the first ninth, within the first tenth, or within the first percent of the length of the test field, as determined starting from the application site of the sample. It is understood by the skilled person that a minimum distance from said application site may be necessary to obtain appropriate detection conditions. In various embodiments, the first measurement value is used as the measurement information, the second measurement value is used as the measurement information, an average value of the first measurement value and the second measurement value is used as the measurement information, or an analyte-induced change of the measurable property is measured in at least one third measurement location of the test field, thereby generating at least one third measurement value, wherein the third measurement value is used as the measurement information.

The term "algorithm" is known in the art and relates to an arithmetical or computational procedure. The evaluation algorithm of the present invention determines the concentration of the analyte by applying a mathematical or graphical representation of the interdependency of analyte concentration in a sample, concentration of a particulate compound in said sample, and the difference between a first and second measurement value to the first and second input variable of the present invention. It is understood by the skilled person that the evaluation algorithm may be any appropriate algorithm, such as an algorithm using a multidimensional calibration surface or a multivariate statistical algorithm, e.g. a partial least squares regression (PLS regression) algorithm. In one embodiment, a plurality of evaluation algorithms is obtained for a plurality of values of at least one additional parameter known or expected to influence the first and/or the second input variable. In other embodiments, said additional parameter is an ambient parameter; in yet other embodiments, the additional parameter is temperature, such as ambient temperature. It is understood by the skilled person that the temperature at the test chemistry is the parameter most profoundly influencing the first and/or second parameter. It is, however, also understood by the skilled person that the mass of the test element and of the sample in conventional test elements are small enough to have ambient temperature by the time of measurement. Thus, the method may comprise a further step of measuring the ambient temperature. It is, however, also envisaged that the method comprises a step of measuring the temperature of the sample and/or of the test chemistry at the time of obtaining the measurement value, and/or that the method comprises a step of adjusting the temperature of the test element, and/or the test chemistry and/or the sample.

In one embodiment, the evaluation algorithm is a one-step algorithm and the first input variable and the second input variable are simultaneously used for deriving the concentration of the analyte in the body fluid by using at least one predetermined calibration surface, the predetermined calibration surface indicating the concentration of the analyte as a function of the two input variables. Thus, said representation of said interdependency may be obtained by measuring the first and second measurement values for various analyte concentrations and at various concentrations of a particulate compound in the sample. This way, a three-dimensional graph representing a calibration surface is obtained. The skilled person knows how to approximate the calibration surface thus obtained by an equation. Thus, having the first and the second input variable at hand, the skilled person can directly determine the corrected value of the analyte concentration, the term "corrected value of the analyte concentration" relating to a value of the analyte concentration corrected for a deviation from the actual value of the analyte concentration caused by the presence of the particulate compound at the given concentration.

It is understood that the same result may be obtained by generating a series of calibration curves instead of a calibration surface. E.g. a series of graphs can be generated, wherein in each of the graphs the signal intensity is correlated to various concentrations of the analyte measured at a given concentration of a particulate compound equivalent to a certain intensity difference between the first and the second measurement location. The best estimation of the concentration of the analyte can then be determined by choosing the curve being closest to the measured intensity difference.

It is to be understood that the above algorithm may also be performed as a two-step-algorithm, wherein the algorithm comprises the two separate steps: in a first step of the algorithm, an estimate value of the concentration is derived from the second input variable by using at least one predetermined first calibration curve, the predetermined first calibration curve indicating an uncorrected concentration of the analyte as a function of the second input variable, and in a second step of the algorithm, the estimate value of the concentration is corrected by applying at least one correction algorithm to the estimate value, the correction algorithm providing a correction to the estimate value by using the first input variable. In one embodiment, the first calibration curve is a mathematical or graphical representation of the interdependency of analyte concentration in a sample and the second variable of the present invention at a fixed concentration of a particulate compound. Thus, said representation of said interdependency may be obtained by obtaining a second variable for various analyte concentrations at a fixed concentration of a particulate compound, such as at a fixed concentration of a particulate compound corresponding to the average concentration of a particulate compound present in a population of subjects. The estimate value thus obtained is then corrected by applying a correction algorithm using the first and the second variable.

It was found in the experiments underlying the present invention that the presence of a particulate component in a sample induces a deviation of measured values from the actual concentration of an analyte along a test element in the flow direction. Moreover, it was found that the deviation (bias) increases with increasing concentration of the particulate compound and with increasing distance from the application site. As a consequence, the gradient along the test element can be used to correct the measured values for the bias induced by the particulate compound; further, the best estimation of the actual concentration of the analyte without correction for said bias is obtained by measuring close to the application site. In particular, it was found in the experiments underlying the present invention that, depending on the hematocrit of a blood sample, a concentration gradient along a test strip occurs, which allows to correct the measured values for the hematocrit.

The definitions made above apply mutatis mutandis to the following:

In a further embodiment, the present invention relates to a method for detecting an analyte in a body fluid, the method having the following steps:

a) applying a sample (122) of the body fluid to a test element (120), said test element (120) comprising at least
  (i) a test field (128) having at least one test material (130) adapted to change at least one measurable property in the presence of the analyte,
  (ii) a capillary element (126) adapted to guide the sample (122) across said test field (128) in a flow direction (146),
  (iii) at least one single measurement location (158) within said test field (128);

b) measuring the measurable property in said single measurement location (158), thereby generating at least one measurement value;

c) detecting the analyte by using an evaluation algorithm having the measurable property as an input variable,
wherein said single measurement location is located within the first third of the test field (128) as determined from the application site.

As used herein, the term "single measurement location" or "single location" relates to a measurement location as defined above located within the first third of the test field (128) as deter-mined from the application site. In various embodiments, the single measurement location is centered within the first quarter, within the first fifth, within the first sixth, within the first seventh, within the first eighth, within the first ninth, within the first tenth, or within the first percent of the length of the test field, as determined starting from the application site of the sample. It is understood by the skilled person that a minimum distance from said application site may be necessary to obtain appropriate detection.

In a further embodiment, the present invention relates to a test device for detecting an analyte in a body fluid, wherein the device contains
  a) at least one test element receptacle for receiving at least one test element, the test element having
    (i) at least one test field having at least one test material adapted to change at least one measurable property in the presence of the analyte and
    (ii) having a capillary element adapted to guide the sample across the test field in a flow direction,
  b) wherein the receptacle is adapted to locate the test element in at least one application position in which a sample of the body fluid is applicable to the test element,
  c) wherein the device further contains at least one detector for measuring the measurable property, wherein the detector is adapted to measure the measurable property
    (i) in at least one first location of the test field, thereby generating at least one first measurement value,
    (ii) in at least one second location of the test field, thereby generating at least one second measurement value, wherein the second location is offset from the first location in the flow direction,
  d) wherein the test device further comprises at least one evaluation unit adapted to determine the concentration of the analyte by using an evaluation algorithm having at least two input variables,
    (i) wherein at least one first input variable of the at least two input variables includes an information on a difference between the first measurement value and the second measurement value, and
    (ii) wherein at least one second input variable of the at least two input variables includes a measurement information on an analyte-induced change of the test material in at least part of the test field.

The test device may be adapted to measure the analyte-induced change of the measurable property in at least two measurement locations as specified herein above. In one embodiment, the test device is further adapted to measure the analyte-induced change of the measurable property in at least one third location of the test field, thereby generating at least a third measurement value. In other embodiments, the measurable property is measured in two locations. The test device further comprises at least one sensor for determining an ambient parameter. For example, the test device may comprise at least one temperature sensor for determining an ambient temperature. In other embodiments, test device is a hand-held test device.

The term "test element receptacle" is known to the skilled person and relates to an element of the device shaped for receiving at least one test element according to the present invention, providing one or more connectors and/or detectors as appropriate for detecting an analyte in a body fluid, and adapted to locate the test element in at least one application position in which a sample of the body fluid is applicable to the test element. The specific embodiment of the test element receptacle will depend on the kind of test element and on the test chemistry used therein, and is a determination well within the capabilities of a skilled person.

The term "detector" is also known to the skilled person. The skilled person, as described above, knows how to use different test chemistries and how to use an appropriate detector for the respective test chemistry. Thus, the detector may be adapted to measure the measurable property of the test chemistry as described herein above. The detector may further include at least one light source for illuminating at least one of the first location and the second location and at least one optically sensitive element adapted to determine detection light from at least one of the first location and the second location.

As used herein, the term "evaluation unit" relates to a unit of a device applying at least one of the algorithms according to the present invention to the first and second input variable as defined herein above. Thus, the evaluation unit is adapted to determine the concentration of the analyte by using an evaluation algorithm having at least two input variables. The evaluation unit further may be adapted to select a measurement value as described herein above, to select an algorithm according to an ambient parameter, and/or to store reference values and or reference curves and/or reference areas. In one embodiment, the evaluation unit is adapted to perform all calculations and evaluations required to print out a value of a concentration of an analyte in a sample in a body fluid. In further embodiments, the evaluation unit is adapted to receive one or more detector signals and to detect and print out a blood glucose level of a sample of blood in a test element inserted in a test element receptacle. In some cases, the evaluation unit comprises at least one data processing device, such as a microcomputer.

In a further embodiment, the present invention relates to a test device (112) for detecting an analyte in a body fluid, wherein the test device (112) contains a) at least one receptacle (118) for receiving at least one test element (120), the test element (120) having (i) at least one test field (128) having at least one test material (130) adapted to change at least one measurable property in the presence of the analyte and (ii) at least one capillary element (126) adapted to guide the sample (122) across the test field (128) in a flow direction (146), b) wherein the receptacle (118) is adapted to locate the test element (120) in at least one application position in which a sample (122) of the body fluid is applicable to the test element (120), c) wherein the device further contains at least one detector (132) for measuring the measurable property, wherein the detector (132) is adapted to measure the measurable property in at least one single measurement location (158) of the test field (128), thereby generating at least one measurement value, d) wherein the test device (112) further comprises at least one evaluation unit (138) adapted to determine the concentration of the analyte by using an evaluation algorithm having at least said measurement value as an input variable, wherein the detector is adapted to measure the measurable property within the first third of the test field.

In another embodiment, the present invention relates to a test system for detecting an analyte in a body fluid, the test system comprising at least one test device according to one of the preceding claims referring to a test device, and at least one test element, wherein the test element has at least one test field having at least one test material adapted to change at least one measurable property in the presence of the analyte and having a capillary element adapted to guide the sample across the test field in a flow direction.

In a further embodiment, the present invention relates to a use of a difference of at least two measurement values measured in at least two different locations of a test field of a test element for generating a corrected value of an analyte concentration in a sample of a body fluid, wherein the sample of the body fluid is guided across the test field by a capillary element in a flow direction, wherein the at least two different locations are offset in the flow direction.

The invention further discloses and proposes a computer program including computer-executable instructions for performing the method according to the present invention in one or more of the embodiments enclosed herein when the program is executed on a computer or computer network. Therein, one, more than one or all method steps of the method may be performed and/or supported by using a computer. Specifically, the computer program may be stored on a computer-readable data carrier.

The invention further discloses and proposes a computer program product having program code means, in order to perform the method according to the present invention in one or more of the embodiments disclosed herein when the program is executed on a computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute the method according to one or more of the embodiments disclosed herein.

The invention further proposes and discloses a computer program product with program code means are stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal containing instructions readable by a computer system or computer network, for performing the method according to one or more of the embodiments disclosed herein.

Referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the embodiments of the present invention further include:

a computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiments, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

Summarizing the findings of the present invention, the following embodiments are disclosed to describe the present invention:

Embodiment 1

A method for detecting an analyte in a body fluid, the method having the following steps:

a) applying a sample of the body fluid to a test element, said test element comprising at least (i) a test field having at least one test material adapted to change at least one measurable property in the presence of the analyte, (ii) a capillary element adapted to guide the sample across said test field in a flow direction, (iii) a first and a second measurement location within said test field, wherein the second measurement location is offset from the first measurement location in the flow direction;

b) measuring the measurable property in said at least one first measurement location, thereby generating at least one first measurement value;

c) measuring the measurable property in said at least one second measurement location, thereby generating at least one second measurement value;

d) detecting the analyte by using an evaluation algorithm having at least two input variables, wherein (i) at least one first input variable of the at least two input variables includes an information on a difference between the first measurement value and the second measurement value, and (ii) at least one second input variable of the at least two input variables includes a measurement information on an analyte-induced change of the measurable property of the test material in at least part of the test field.

Embodiment 2

The method according to the preceding embodiment, wherein the measurement information on an analyte-induced change of the measurable property of the test material in at least part of the test field is generated by one or more of the following procedures:

the first measurement value is used as the measurement information;

the second measurement value is used as the measurement information;

an average value of the first measurement value and the second measurement value is used as the measurement information;

an analyte-induced change of the measurable property is measured in at least one third measurement location of the test field, thereby generating at least one third measurement value, wherein the third measurement value is used as the measurement information.

Embodiment 3

The method according to one of the preceding embodiments, wherein the measurement information used in step d) (ii) is a measurement value generated at a measurement location located within one of the first 75% of the test field in view of the flow direction, the first half of the test field, within the first third of the test field, and within the first quarter of the test field.

Embodiment 4

The method according to one of the preceding embodiments, wherein method steps b) and c) are performed a predetermined time span after application of the sample of the body fluid to the test element; or at a point in time at which a measurement curve indicating the measurable property as a function of time fulfills at least one predetermined condition, such as least one threshold condition wherein a slope of the measurement curve is below or above a predetermined threshold.

Embodiment 5

The method according to one of the preceding embodiments, wherein the evaluation algorithm comprises a one-step evaluation algorithm, and the first input variable and the second input variable are simultaneously used for deriving the concentration of the analyte in the body fluid by using at least one predetermined calibration curve, the predetermined calibration curve indicating the concentration of the analyte as a function of the two input variables.

Embodiment 6

The method according to one of the preceding embodiments, wherein the evaluation algorithm comprises at least two separate steps, in a first step of the algorithm an estimate value of the concentration is derived from the second input variable by using at least one predetermined first calibration curve, the predetermined first calibration curve indicating an uncorrected concentration of the analyte as a function of the second input variable, and in a second step of the algorithm the estimate value of the concentration is corrected by applying at least one correction algorithm to the estimate value, the correction algorithm providing a correction to the estimate value by using the first input variable.

Embodiment 7

The method according to the preceding embodiment, wherein
the sample of the body fluid is blood,
in the first step of the algorithm, an estimate value of a glucose concentration is generated, and
in the second step of the algorithm, a correction of the estimate value for an actual hematocrit of the blood is provided, thereby generating an information on the glucose concentration in the blood without determining the actual hematocrit of the blood.

Embodiment 8

The method according to one of the preceding embodiments, wherein, in method step d), the at least one first input variable includes an information on a gradient of measurement values over at least part of the test field.

Embodiment 9

The method according to the preceding embodiment, wherein the gradient is a gradient in the flow direction.

Embodiment 10

The method according to one of the preceding embodiments, wherein, in method step d), the evaluation algorithm is chosen from a set of evaluation algorithms, wherein the choice is made in accordance with at least one ambient parameter.

Embodiment 11

The method according to the preceding embodiment, wherein the ambient parameter is an ambient temperature, wherein the set of evaluation algorithms contains a plurality of evaluation algorithms for different ambient temperatures.

Embodiment 12

The method according to the preceding embodiment, wherein the method further comprises at least one method step of measuring the ambient temperature.

Embodiment 13

The method according to one of the preceding embodiments, wherein the test material comprises at least one enzyme adapted for performing at least one enzymatic reaction in the presence of the analyte.

Embodiment 14

The method according to the preceding embodiment, wherein the enzyme comprises at least one of glucose oxidase and glucose dehydrogenase.

Embodiment 15

The method according to one of the preceding embodiments, wherein the first measurement value and the second measurement value are selected from the group consisting of: an optical measurement value, such as remission; an electrical measurement value, such as current and/or a voltage.

Embodiment 16

The method according to one of the preceding embodiments, wherein the test element is selected from an optical test element and an electrochemical test element.

Embodiment 17

The method according to one of the preceding embodiments, wherein the test material is adapted to change at least one optical property in the presence of the analyte.

Embodiment 18

The method according to the preceding embodiment, wherein the optical property is selected from the group consisting of: a reflection property, such as a reflectance and/or a remission; transmission property, such as an absorption; a color; a luminescence, such as a fluorescence.

Embodiment 19

The method according to one of the two preceding embodiments, wherein at least one of method steps b) and c) implies using at least one detector for generating the measurement value.

Embodiment 20

The method according to the preceding embodiment, wherein the detector includes at least one light source for illuminating at least one of the first location and the second location and at least one optically sensitive element adapted to determine detection light from at least one of the first location and the second location.

Embodiment 21

The method according to the preceding embodiment, wherein the detection light is selected from the group consisting of: light reflected by the test field in at least one of the first location and the second location, light transmitted by the test field in at least one of the first location and the second location, light emitted by the test field in at least one of the first location and the second location.

Embodiment 22

The method according to one of the two preceding embodiments, wherein the optically sensitive element comprises at least one one-dimensional or two-dimensional matrix of optically sensitive elements, such as at least one camera chip or at least one CCD chip.

Embodiment 23

The method according to one of the six preceding embodiments, wherein, in method steps b) and c), the at least one first location and the at least one second location are illuminated by one of: light having the same wavelengths, light having different wavelengths.

Embodiment 24

The method according to one of the seven preceding embodiments, wherein, in method steps b) and c), the at least one first location and the at least one second location are illuminated by modulated light having different modulation frequencies.

Embodiment 25

The method according to one of the preceding embodiments, wherein the body fluid is selected from the group consisting of: blood, plasma, urine and saliva.

Embodiment 26

The method according to one of the preceding embodiments, wherein the analyte is a chemical compound with a molecular mass of less than 1000 u (1000 Da; 1.66×10-24 kg) or is selected from the group consisting of: glucose, lactate, cholesterol, and triglycerides.

Embodiment 27

The method according to one of the preceding embodiments, wherein the test element is a test strip.

Embodiment 28

The method according to one of the preceding embodiments, wherein the test field has a multilayer setup, the multilayer setup comprising at least one detection layer having the at least one test material and further comprising at least one separation layer adapted for separating off at least one particulate component contained in the body fluid, wherein the separation layer is located between the detection layer and the capillary element.

Embodiment 29

The method according to one of the preceding embodiments, wherein the capillary element comprises at least one capillary slit extending across at least a part of the test field.

Embodiment 30

The method according to the preceding embodiment, wherein the capillary slit is formed by a surface of the test field and a guide surface disposed at a distance above the surface of the test field.

Embodiment 31

The method according to the preceding embodiment, wherein the guide surface is formed by a surface of a cover plate being disposed above the surface of the test field.

Embodiment 32

The method according to one of the three preceding embodiments, wherein the capillary slit has a width selected from one of the ranges including 30 µm to 300 µm, 40 µm to 200 µm, 50 µm to 100 µm, and 60 µm to 80 µm, or a width of 70 µm.

Embodiment 33

The method according to one of the preceding embodiments, wherein the test field is applied to a substrate on a surface of the substrate facing the capillary element, wherein the substrate contains at least one detection window, wherein in method steps b) and c), the measurable property is measured through the detection window.

Embodiment 34

A test device for detecting an analyte in a body fluid, wherein the device contains
a) at least one test element receptacle for receiving at least one test element, the test element having
  (i) at least one test field having at least one test material adapted to change at least one measurable property in the presence of the analyte and
  (ii) having a capillary element adapted to guide the sample across the test field in a flow direction,
b) wherein the receptacle is adapted to locate the test element in at least one application position in which a sample of the body fluid is applicable to the test element,
c) wherein the device further contains at least one detector for measuring the measurable property, wherein the detector is adapted to measure the measurable property
  (i) in at least one first location of the test field, thereby generating at least one first measurement value,
  (ii) in at least one second location of the test field, thereby generating at least one second measurement value, wherein the second location is offset from the first location in the flow direction,
d) wherein the test device further comprises at least one evaluation unit adapted to determine the concentration of the analyte by using an evaluation algorithm having at least two input variables,
  (i) wherein at least one first input variable of the at least two input variables includes an information on a difference between the first measurement value and the second measurement value, and
  (ii) wherein at least one second input variable of the at least two input variables includes a measurement information on an analyte-induced change of the test material in at least part of the test field.

Embodiment 35

The test device according to the preceding embodiment, wherein the test device is adapted to perform the method according to one of the preceding method embodiments.

Embodiment 36

The test device according to one of the preceding embodiments referring to a test device, wherein the at least one first input variable includes an information on a gradient of measurement values over at least part of the test field.

Embodiment 37

The test device according to the preceding embodiment, wherein the gradient is a gradient in the flow direction.

Embodiment 38

The test device according to one of the preceding embodiments referring to a test device, wherein
  the test device is adapted to measure the analyte-induced change of the measurable property in at least one third location of the test field, thereby generating at least one third measurement value,
  the third measurement value is used as the measurement information, the test field extends in the flow direction, and wherein the third location is located within the first 75% or the first half of the test field in view of the flow direction, within the first third of the test field, or within the first quarter of the test field.

Embodiment 39

The test device according to one of the preceding embodiments referring to a test device, wherein the evaluation unit comprises at least one data processing device, such as a microcomputer.

Embodiment 40

The test device according to one of the preceding embodiments referring to a test device, wherein the test device is a hand-held test device.

Embodiment 41

The test device according to one of the preceding embodiments referring to a test device, wherein the test device further comprises at least one temperature sensor for determining an ambient temperature.

Embodiment 42

The test device according to one of the preceding embodiments referring to a test device, wherein the first measurement value and the second measurement value are selected from the group consisting of: an optical measurement value, such as a remission; an electrical measurement value, such as a current and/or a voltage.

Embodiment 43

The test device according to one of the preceding embodiments referring to a test device, wherein the test element is selected from an optical test element and an electrochemical test element.

Embodiment 44

The test device according to one of the preceding embodiments referring to a test device, wherein the detector includes
at least one light source for illuminating at least one of the first location and the second location, and
at least one optically sensitive element adapted to measure detection light from at least one of the first location and the second location.

Embodiment 45

The test device according to the preceding embodiment, wherein the detection light is selected from the group consisting of: light reflected by the test field in at least one of the first location and the second location, light transmitted by the test field in at least one of the first location and the second location, light emitted by the test field in at least one of the first location and the second location.

Embodiment 46

The test device according to one of the two preceding embodiments, wherein the optically sensitive element comprises at least one one-dimensional or two-dimensional matrix of optically sensitive elements, such as a camera chip or a CCD chip.

Embodiment 47

The test device according to one of the preceding embodiments referring to a test device, wherein the detector is adapted to illuminate the at least one first location and the at least one second location by one of: light having the same wavelengths, light having different wavelengths.

Embodiment 48

A test system for detecting an analyte in a body fluid, the test system comprising
a) at least one test device according to one of the preceding embodiments referring to a test device, and
b) at least one test element, wherein the test element has at least one test field having at least one test material adapted to change at least one measurable property in the presence of the analyte and having a capillary element adapted to guide the sample across the test field in a flow direction.

Embodiment 49

The test system according to the preceding embodiment, wherein the test element is selected from the group consisting of: a test strip, a test tape, a test disc.

Embodiment 50

The test system according to one of the preceding embodiments referring to a test system, wherein the test material comprises at least one enzyme adapted for performing at least one enzymatic reaction in the presence of the analyte.

Embodiment 51

The test system according to the preceding embodiment, wherein the enzyme comprises at least one of glucose oxidase and glucose dehydrogenase.

Embodiment 52

The test system according to one of the preceding embodiments referring to a test system, wherein the test material is adapted to change at least one optical property in the presence of the analyte.

Embodiment 53

The test system according to the preceding embodiment, wherein the optical property is selected from the group consisting of: a reflection property, such as a reflectance and/or a remission; transmission property, such as an absorption; a color; a luminescence, such as a fluorescence.

Embodiment 54

The test system according to one of the preceding embodiments referring to a test system, wherein the body fluid is selected from the group consisting of: blood, plasma, urine and saliva.

Embodiment 55

The test system according to one of the preceding embodiments referring to a test system, wherein the analyte is a chemical compound with a molecular mass of less than 1000 u (1000 Da; 1.66×10-24 kg), or is selected from the group consisting of: glucose, lactate, cholesterol, and triglycerides.

Embodiment 56

The test system according to one of the preceding embodiments referring to a test system, wherein the test element is a test strip.

Embodiment 57

The test system according to one of the preceding embodiments referring to a test system, wherein the test field has a multilayer setup, the multilayer setup comprising at least one detection layer having the at least one test material and further comprising at least one separation layer adapted for separating off at least one particulate component contained in the body fluid, wherein the separation layer is located between the detection layer and the capillary element.

Embodiment 58

The test system according to one of the preceding embodiments referring to a test system, wherein the capillary element comprises at least one capillary slit extending across at least a part of the test field.

Embodiment 59

The test system according to one of the preceding embodiments referring to a test system, wherein the capillary slit is formed by a surface of the test field and a guide surface disposed at a distance above the surface of the test field.

Embodiment 60

The test system according to the preceding embodiment, wherein the guide surface is formed by a surface of a cover plate being disposed above the surface of the test field.

Embodiment 61

The test system according to one of the three preceding embodiments, wherein the capillary slit has a width selected from one of the ranges including 30 μm to 300 μm, 40 μm to 200 μm, 50 μm to 100 μm, and 60 μm to 80 μm, or a width of 70 μm.

Embodiment 62

The test system according to one of the preceding embodiments referring to a test system, wherein the test field is applied to a substrate on a surface of the substrate facing the capillary element, wherein the substrate contains at least one detection window, wherein the test device is adapted to measure the measurable property through the detection window.

Embodiment 63

The test system according to one of the preceding embodiments referring to a test system, wherein the capillary element comprises at least one application opening, wherein the capillary element is adapted to guide the body fluid from the application opening to the test field.

Embodiment 64

The test system according to the preceding embodiment, wherein the capillary element is adapted to guide the body fluid by capillary forces.

Embodiment 65

The test system according to one of the two preceding embodiments, wherein the application opening is located at a front face of the test element.

Embodiment 66

A use of a difference of at least two measurement values measured in at least two different locations of a test field of a test element for generating a corrected value of an analyte concentration in a sample of a body fluid, wherein the sample of the body fluid is guided across the test field by a capillary element in a flow direction, wherein the at least two different locations are offset in the flow direction.

Embodiment 67

The use according to the preceding embodiment, wherein the corrected value is dependent on the concentration of a particulate component in the body fluid, such as hematocrit.

In FIG. 1, a cross-sectional view of an embodiment of a test device 112 and a test system 114 according to the present invention is depicted. The test device 112, may be embodied as a hand-held device. The test device 112 comprises a casing 116, which may have a volume of less than 1000 cm$^3$, or even less than 500 cm$^3$, in order to be carried by a person. The test device 112 comprises a receptacle 118 for receiving a test element 120, which, besides the test device 112, forms a component of the test system 114. The receptacle is adapted to locate the test element 120 in at least one application position in which a sample 122 of the body fluid is applicable to the test element 120, such as to an application opening 124 of a capillary element 126, which will be explained in further detail below. The test element 120 comprises at least one test field 128 having at least one test material 130 adapted to change at least one measurable property in the presence of an analyte to be detected by the test system 114, such as glucose.

The test device 112 further comprises a detector 132 which, in this specific embodiment, comprises at least one light source 134 for illuminating the test field 128 and at least one optically sensitive element 136 adapted to measure detection light emitted and/or transmitted and/or reflected from the test field 128.

The test device 112 further comprises at least one evaluation unit 138 which is adapted to determine the concentration of the analyte by using the evaluation algorithm as disclosed above or as disclosed in further detail below. The evaluation unit 138 may be or may comprise at least one data processing device, such as at least one computer and/or at least one application-specific integrated circuit. As an example, the evaluation unit 138 may comprise a microcomputer. Further, the evaluation unit 138 may comprise one or more further elements, such as at least one data storage device and/or other components.

The evaluation unit 138 is unidirectionally or bidirectionally connected to the detector 132, such as for receiving measurement values from the detector 132. Further, the evaluation unit 138 may be adapted to control the overall functionality of the test device 112, such as for controlling the measurement process performed by the detector 132.

The test device 112 may further comprise one or more human-machine-interfaces, such as at least one display 140 and/or at least one control element 142, such as at least one push button. The elements 140, 142 may also be connected to the evaluation unit 138.

The test device 112 may further comprise one or more additional sensors for detecting one or more ambient parameters, such as one or more temperature sensors 145 adapted for determining an ambient temperature. As outlined above, these one or more ambient parameters may be used by the evaluation unit 138 for choosing an appropriate algorithm.

The test device 112 may further comprise at least one electronic interface 144, for unidirectional and/or bidirectional exchange of data and/or commands with one or more external devices, such as a wireless and/or a wire-based interface.

Figure 2:
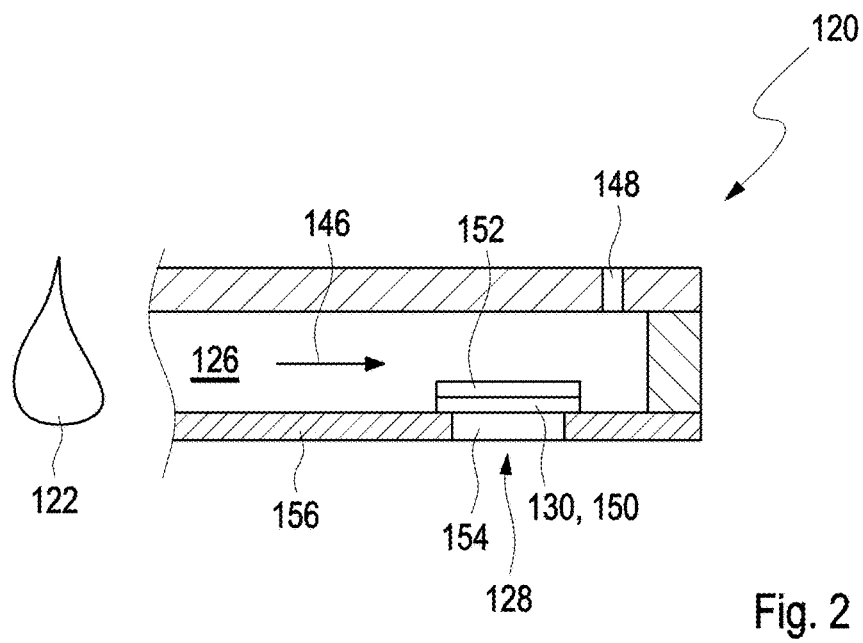
FIG. 2 shows a schematic cross-sectional view of a test element for use in the test system according to FIG. 1.

In FIG. 2, a cross-sectional view of an exemplary embodiment of a test element 120 is depicted. In this exemplary embodiment, the test element 120 is designed as a test strip. However, additionally or alternatively, other types of test elements 120 may be used, such as test tapes and/or test discs.

The test element 120, as outlined above, comprises at least one test field 128 and at least one capillary element 126. The capillary element 126 is adapted to guide the sample 122 of the body fluid across the test field 128 in a flow direction 146. Thus, the capillary element 126 may suck the sample 122 over the test field 128 by capillary forces. For improving the capillary forces, the test element 120 may further comprise one or more venting openings 128.

The test field 128 comprises at least one detection layer 150 comprising the at least one test material 130. The test field 128 may further comprise one or more additional layers, such as at least one separation layer 152 covering the detection layer 150 on the side facing the capillary element 126. The separation layer 152 may comprise one or more pigments, and may include inorganic pigments, such as an inorganic oxide, which may provide a wide optical background for optical measurement. Further, the separation layer 152 may be adapted for separating off at least one particular component contained in the body fluid.

The test element 120 comprises at least one detection window in a substrate 156, through which a change of optical properties in the test field 128 may be detected by using the detector 132. It shall be noted that, in the embodiment depicted in FIG. 2, an optical test element 120 is depicted, in which the test material 130 is adapted to change at least one optical property in the presence of the analyte to be detected. Additionally or alternatively, other types of test elements 120 may be used, such as electrochemical test elements 120, in which the at least one test material 130 is adapted to change at least one electrochemical property in the presence of the analyte to be detected. In the latter case, the test field 128 may comprise one or more electrodes adapted for providing appropriate voltage signals and/or current signals which may be used for generating appropriate measurement values.

In FIGS. 3A to 3D, four different potential setups of the detector 132 of the test device 112 according to FIG. 1 are depicted. According to the present invention, the detector is adapted for measuring at least one optical property, such as at least one remission characteristics, of the test field 128 in at least two different locations of the test field 128. In FIGS. 3A to 3D, symbolically, a first location is denoted by reference number 158, and a second location symbolically is denoted by reference number 160. The locations 158, 160 are offset in the direction of the flow direction 146, which is also symbolically depicted in FIG. 3C.

For measuring the optical property of the test field 128 in the first location 158 and the second location 160, various techniques are feasible. Thus, in FIG. 3A, a setup is depicted in which the detector 132 comprises a first light source 162 and a second light source 164, wherein the first light source 162 illuminates the first location 158, and wherein the second light source 164 is adapted to illuminate the second location 160. The first and second light sources 162, 164 may, as an example, comprise one or more light-emitting devices such as one or more light-emitting diodes. Other types of light sources are feasible. The first and second light sources 162, 164 may be adapted to illuminate the first and second locations, respectively, with light having the same wavelengths and/or light having different wavelengths. Thus, the optical properties of light emitted by the first and second light sources 162, 164 may be identical or may differ. Further, optionally, the first and second light sources 162, 164 may emit light at the same time or may emit light at different points in time, such as by using an intermitting timing schedule.

The detector 132 further may comprise a first optically sensitive element, which is adapted to detect light emitted by the first light source 162 and reflected and/or transmitted by the test field 128 in the first location 158 and at least one second optically sensitive element 168, adapted to detect light emitted by the second light source 164 and reflected and/or transmitted by the test field 128 in the second location 160. It shall be noted that the optically sensitive elements 166, 168 may be adapted to receive light scattered in the first and second locations 158, 160, respectively, such as by measuring a remission value in these locations 158, 160. Other measurement setups are possible in addition or alternatively. Thus, transmission light may be detected and/or the light sources 162, 164 may be adapted to stimulate an emission of light in the test field 128, such as fluorescence and/or phosphorescence.

Figure 3:
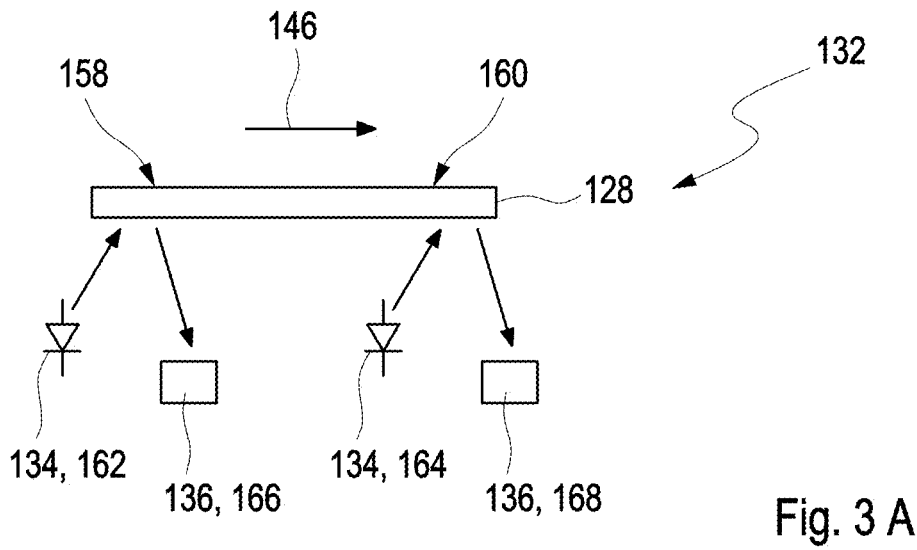
FIGS. 3A-D show different embodiments of detector setups for measuring remission values in at least two different locations of a test field.
Figure 3:
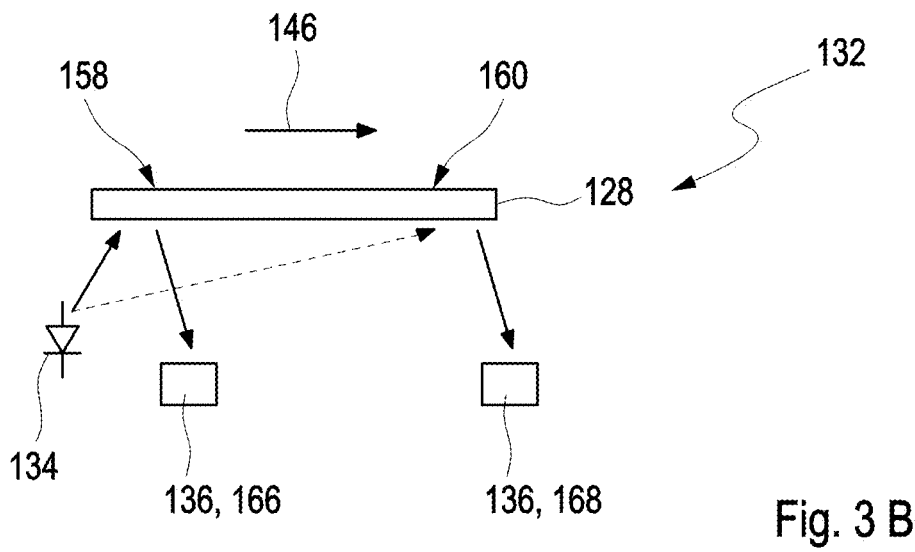
Figure 3:
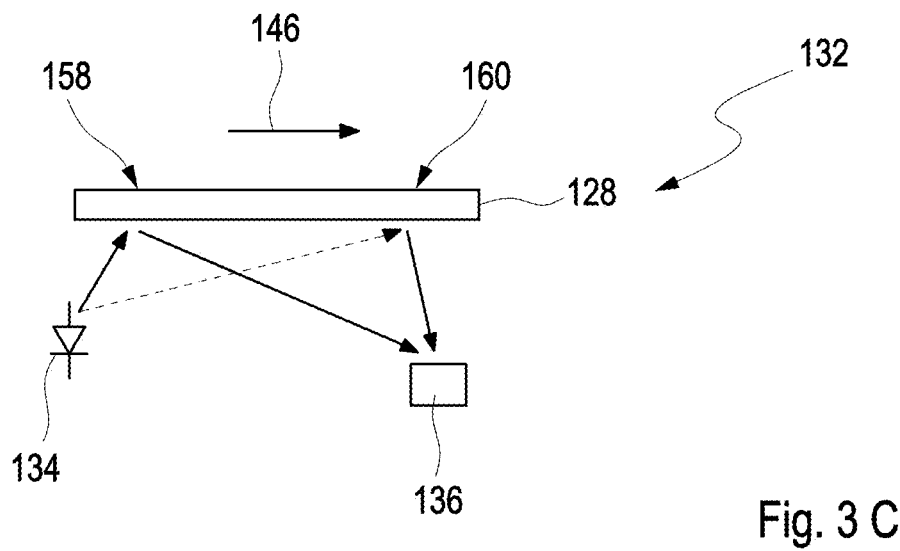
Figure 3:
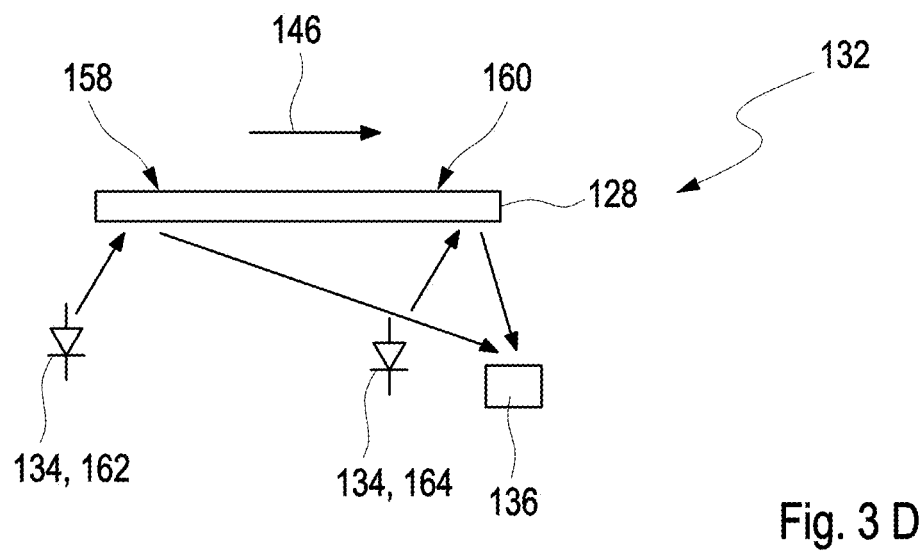

In FIG. 3B, a modification of the setup of FIG. 3A is depicted, in which only one light source 134 is used for illuminating the at least one first location 158 and the at least one second location 160. Still, first and second optically sensitive elements 166, 168 are used for detecting light from the first location 158 and the second location 160, respectively. As in FIG. 3A, the optically sensitive elements 166, 168 may be or may comprise an arbitrary type of optically sensitive element, such as a photodiode. Additionally or alternatively, a camera may be used, as will be explained in further detail below. Other embodiments are possible.

In FIG. 3C, a further modification of the setup shown in FIG. 3A is depicted. In this setup, only one light source 134 and only one optically sensitive element 136 is used for detecting light from the first and second locations 158, 160. Various measurement setups for fulfilling this purpose are feasible. Thus, an optical switch may be provided in order to subsequently illuminate the first and second locations 158, 160 at different points in time by using the same light source 134. Thereby, by using an intermitting timing scheme, light detected by the optically sensitive element 136 at a specific point in time may be allocated to one of the first and second positions 158, 160. Additionally or alternatively, the optically sensitive element 136 may be adapted to spatially resolve the detected light, in order to spatially distinguish between light from the first location 158 and light from the second location 160. Thus, as outlined above and as outlined in further detail below, the optically sensitive element 136 may be or may comprise a camera and/or a camera chip, such as a CCD chip.

In FIG. 3D, a further modification of the setup shown in FIG. 3A is depicted. In this setup, two light sources 134 and only one optically sensitive element 136 is used for detecting light from the first and second locations 158, 160. Various measurement setups for fulfilling this purpose are feasible. The light sources may be triggered subsequently to illuminate the first and second locations 158, 160 at different points in time. Thereby, by using an intermitting timing scheme, light detected by the optically sensitive element 136 at a specific point in time may be allocated to one of the first and second positions 158, 160. Additionally or alternatively, the optically sensitive element 136 may be adapted to spatially resolve the detected light, in order to spatially distinguish between light from the first location 158 and light from the second location 160. Thus, as outlined above and as outlined in further detail below, the optically sensitive element 136 may be or may comprise a camera and/or a camera chip, such as a CCD chip.

Figure 4:
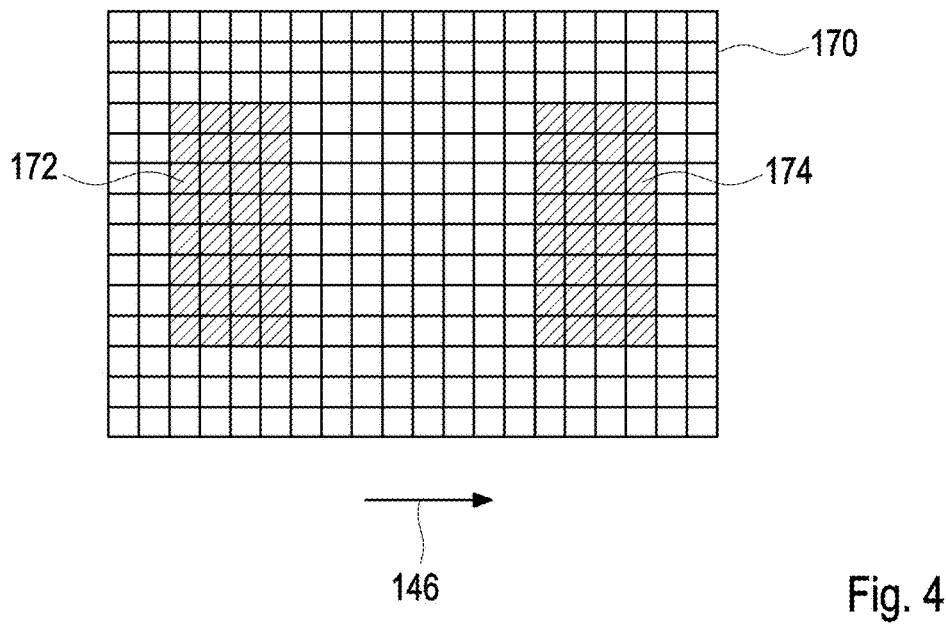
FIG. 4 shows a schematic view of an image of a test field taken by a camera, wherein two different areas of the image are chosen for generating remission values in at least two different locations of the test field.

An embodiment of FIG. 3C or D is schematically depicted in FIG. 4. In this embodiment, an image 170 of the test field 128 captured at a specific point in time is shown, wherein, again, reference number 146 schematically shows the flow direction of the body fluid 122 in the image 170. In the image 170, a first area 172 is marked, which corresponds to pixels of the image representing the first location 158, and a second area 174 is marked, which may contain pixels of the image 170 corresponding to the second location 160.

Figure 5:
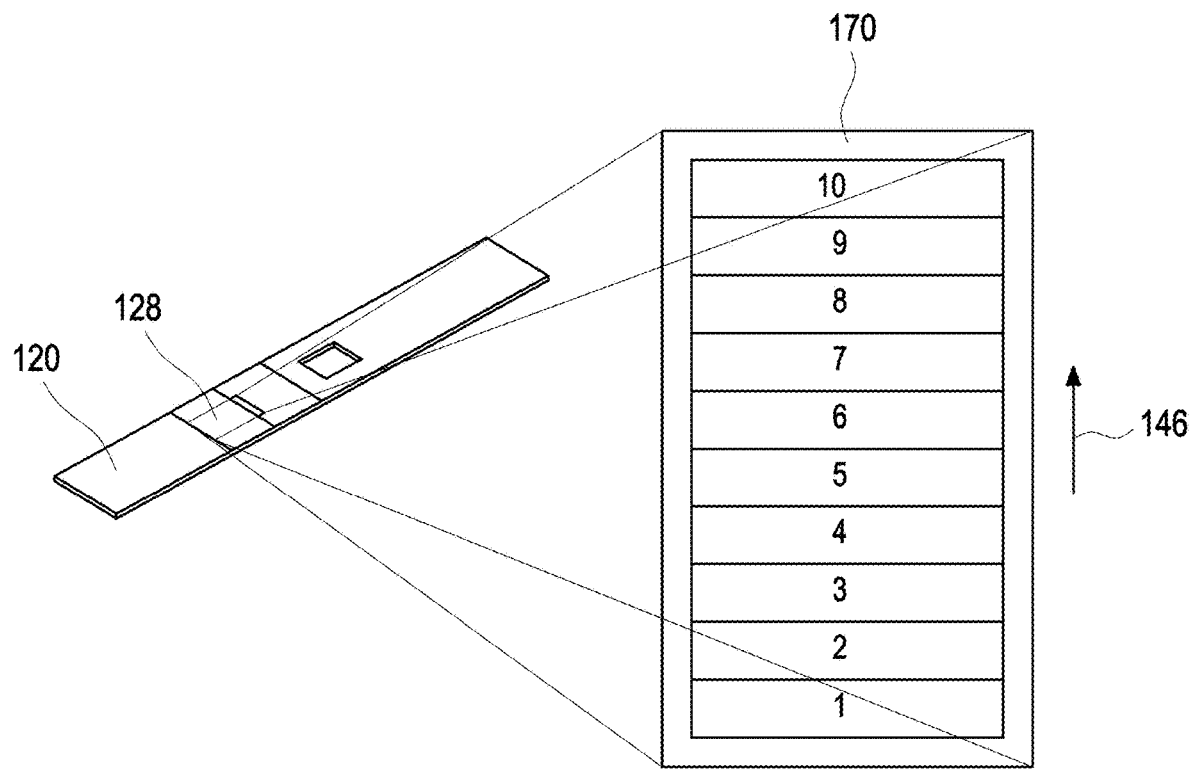
FIG. 5 shows an exemplary embodiment of sub-dividing the test field into different locations (subwindows 1 through 10) along a flow path of a sample.
Figure 6:
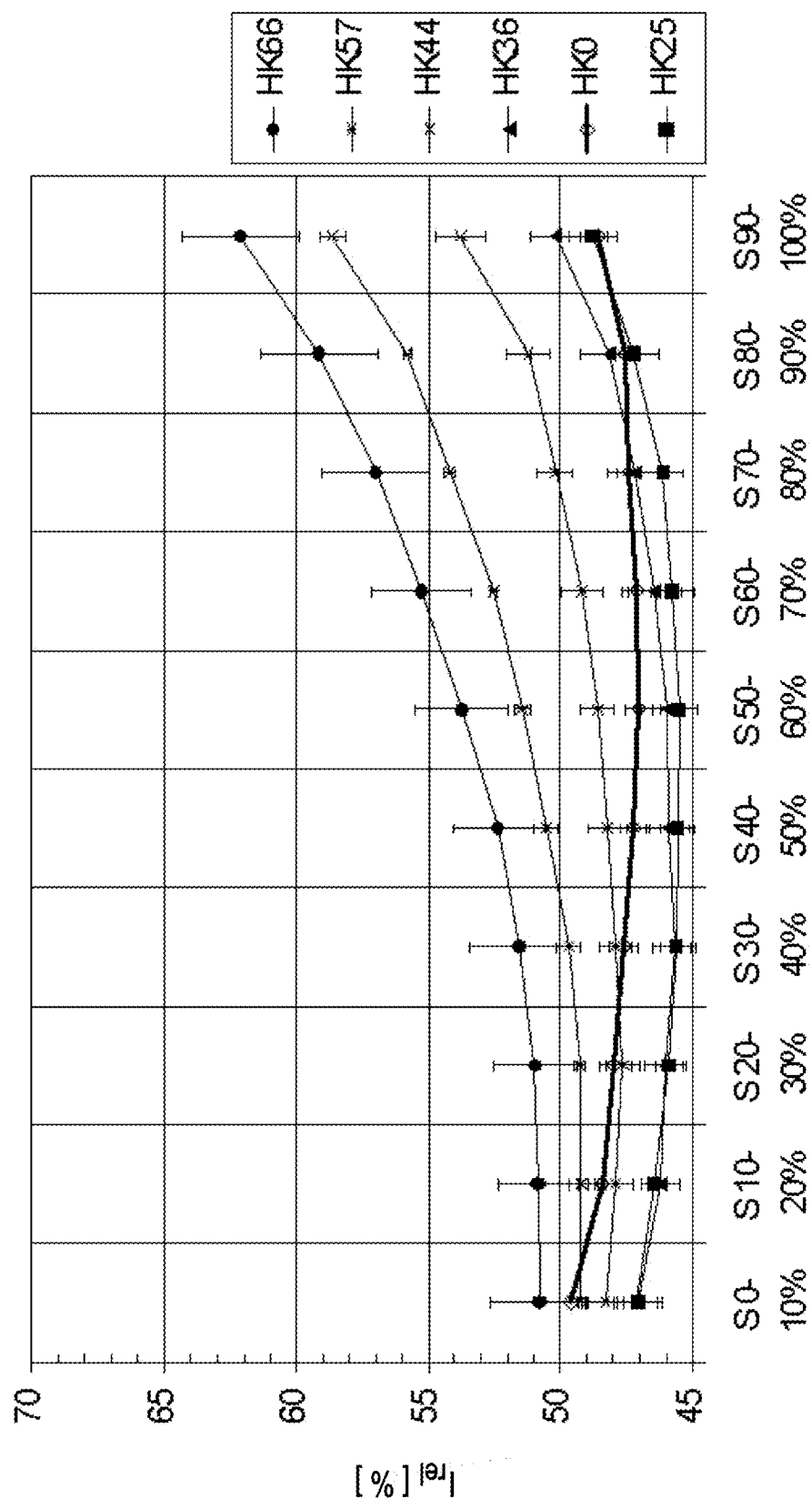
FIG. 6 is a graph showing the measured relative signal intensity ($I_{rel}$) along the test field for various hematocrit (HK) values at a glucose concentration of 200 mg/ml, wherein % values in the labels of the abscissa relate to the percentage of the total length of the test field in flow direction spanned by a respective measurement location.
Figure 7:
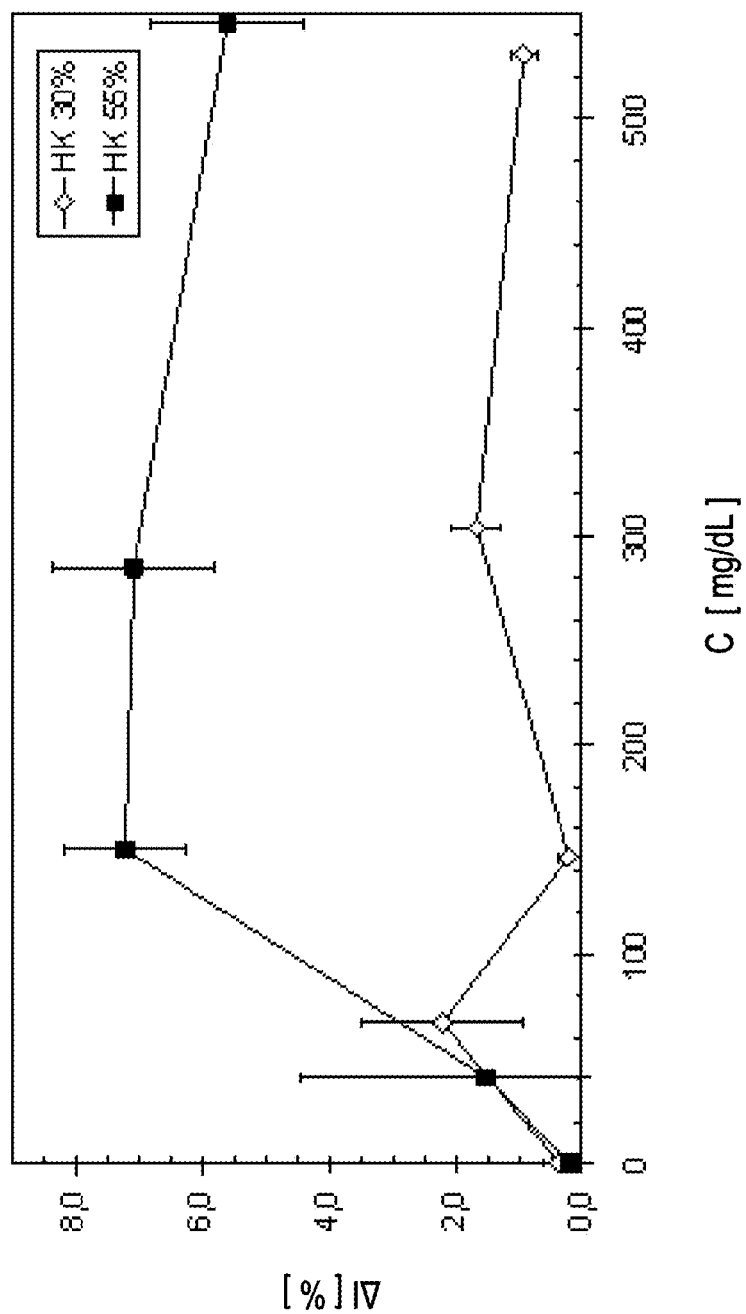
FIG. 7 is a graph showing the dependence of the measurable intensity difference ($\Delta I$) between sub-window 10 and subwindow 2 as shown in FIG. 5 on glucose concentration at two different hematocrit values.
Figure 8:
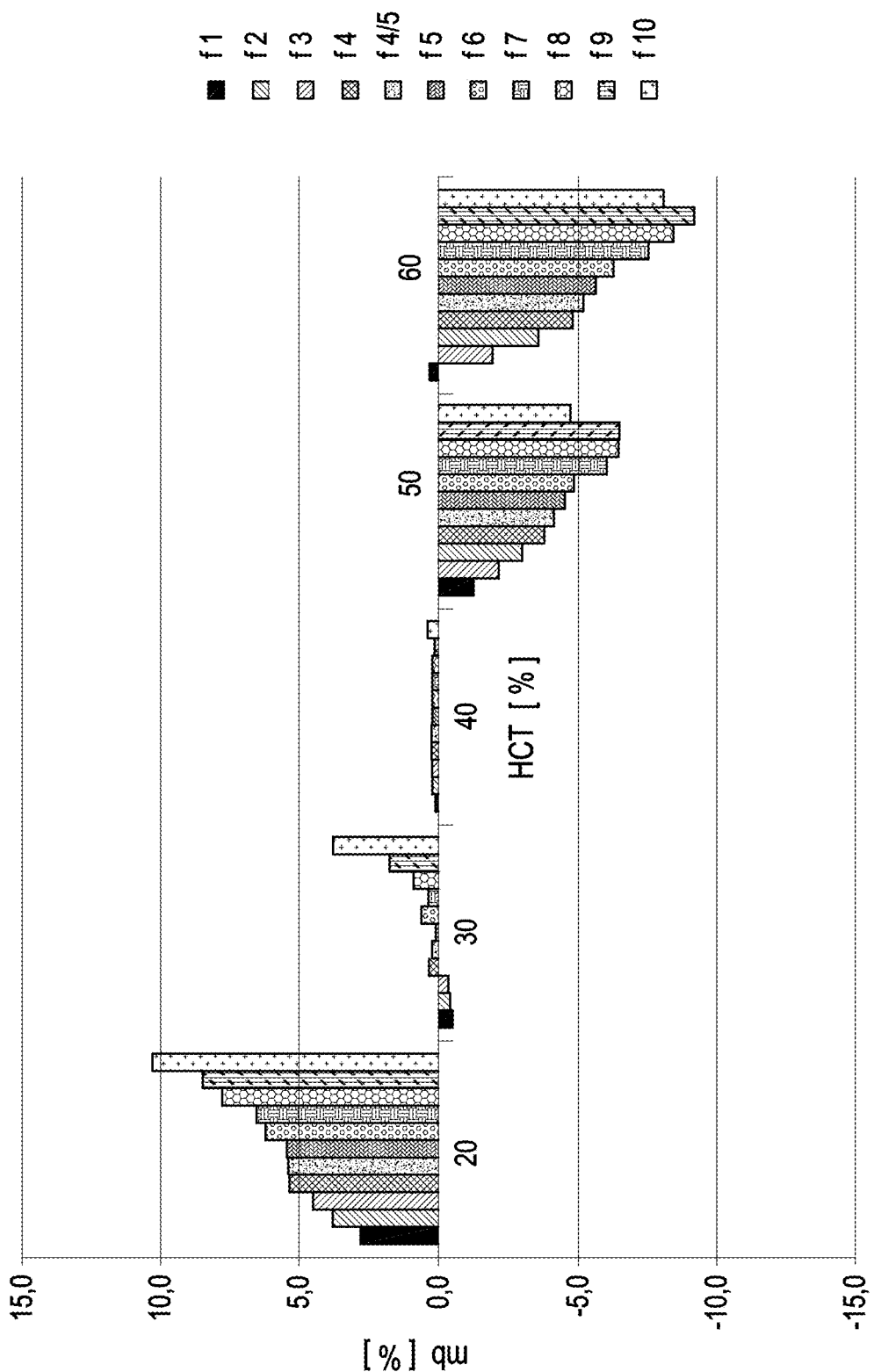
FIG. 8 is a graph showing dependence of the deviation of the glucose concentration as determined from a calibration curve from the actual glucose concentration (mean bias mb, vertical axis) on the position of the measurement location (f1 to f10, f4/5 being the mean value of f4 and f5) and on the hematocrit (HCT) of the sample.
Figure 9:
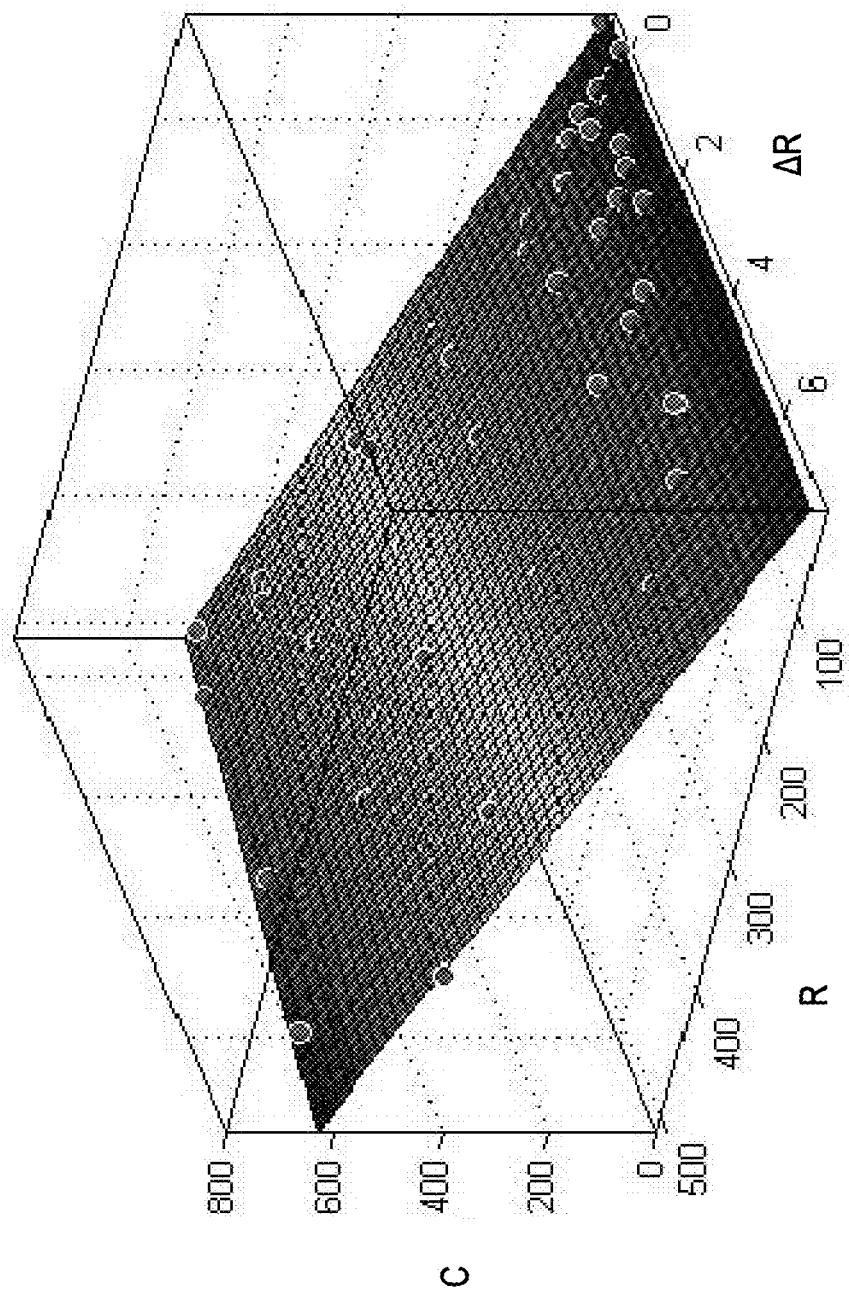
FIG. 9 is a 3-D graph showing dependence of the actual glucose concentration (c) in a blood sample on the linearized remission (R) measured at measurement location subwindow 8 and the remission difference between the two measurement locations subwindow 10 and subwindow 8 ($\Delta R$) using SCV chemistry.

In FIG. 5, a different way of sub-dividing the test field 128 is shown. Therein, an image 170 of the test field 128 is sub-divided into ten different areas, numbered by 1 to 10 in FIG. 5. An arbitrary one of the areas 1 to 10 in FIG. 5 may be chosen as the first location 158 and/or as the first area 172. Further, a combination of areas may be used for the first location 158 and/or the first area 172. Similarly, an arbitrary area of the areas 1 to 10 or a combination of areas of the areas 1 to 10 of FIG. 5 may be chosen as the second location 160 and/or the second area 174, as long as the second area is offset from the first area in the flow direction 146.

In the following, several measurements will be shown for demonstrating that optical measurement values taken in the first location 158 and the second location 160 and differences between these measurement values may be used for correcting the analyte concentration for a hematocrit of the body fluid. Therein, different types of test materials 130 were used. Generally, with regard to test materials 130 usable for the present invention, reference may be made to the prior art documents listed above. Further, reference may be made to J. Hoenes et al.: The Technology Behind Glucose Meters: Test Strips, Diabetes Technology & Therapeutics, vol. 10, Supplement 1, 2008, S-10 to S-26. Additionally or alternatively, other types of test materials 130 may be used. Thus, in the following, reference will be made to the following types of test material:

Firstly, a test material was used which also is referred to as "SCV chemistry". This SCV test chemistry is disclosed e.g. in EP 0 354 441 A2 and may contain a PQQ-dependent dehydrogenase and a direct electron acceptor which may be an aromatic nitroso compound or an oxim. Further, one or more indicators may be present, such as one or more dyes. Thus, as an example, heteropoly blue indicator may be used, as disclosed in EP 0 431 456 A1.

As a second type of test material 130, also referred to as "cNAD chemistry", the test material as disclosed in WO 2007/012494 A1, WO 2009/103540 A1, WO 2011/012269 A2, WO 2011/012270 A1 and WO 2011/012271 A2 is disclosed. Thus, in WO 2007/012494 A1, cNAD derivatives are disclosed. In WO 2009/103540 A1, stabilized enzyme/coenzyme complexes are disclosed. In WO 2011/012269 A2, WO 2011/012270 A1 and WO 2011/012271 A2, the synthesis of cNAD and cNAD/derivatives as well as intermediates/precursors is disclosed.

Measurements were performed at 10 glucose concentrations: 0 mg/dl, 25 mg/dl, 50 mg/dl, 75 mg/dl, 100 mg/dl, 150 mg/dl, 250 mg/dl, 350 mg/dl, 450 mg/dl, 550 mg/dl, and at 5 hematocrit values for every glucose concentration: 20%, 30%, 42%, 50%, 60%; Measurements were repeated 10 times, using a test field of 2.07 mm length in flow direction, and a width of 1.76 mm.

Figure 10:
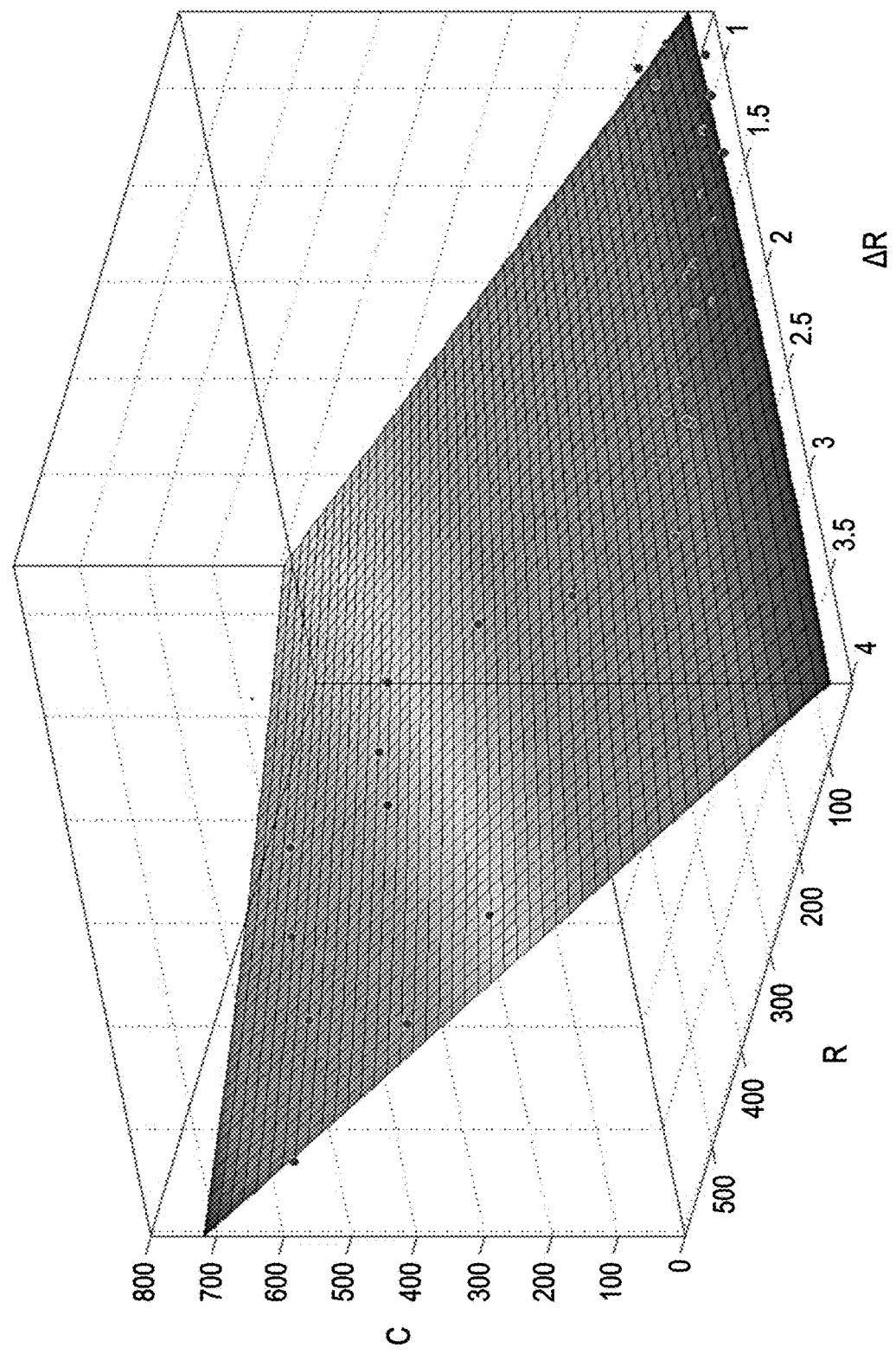
FIG. 10 is a 3-D graph showing dependence of the actual glucose concentration (c) in a blood sample on the linearized remission measured at measurement location subwindow 8 (R) and the difference between the two measurement locations subwindow 10 and subwindow 8 ($\Delta R$) using cNAD chemistry.
Figure 11:
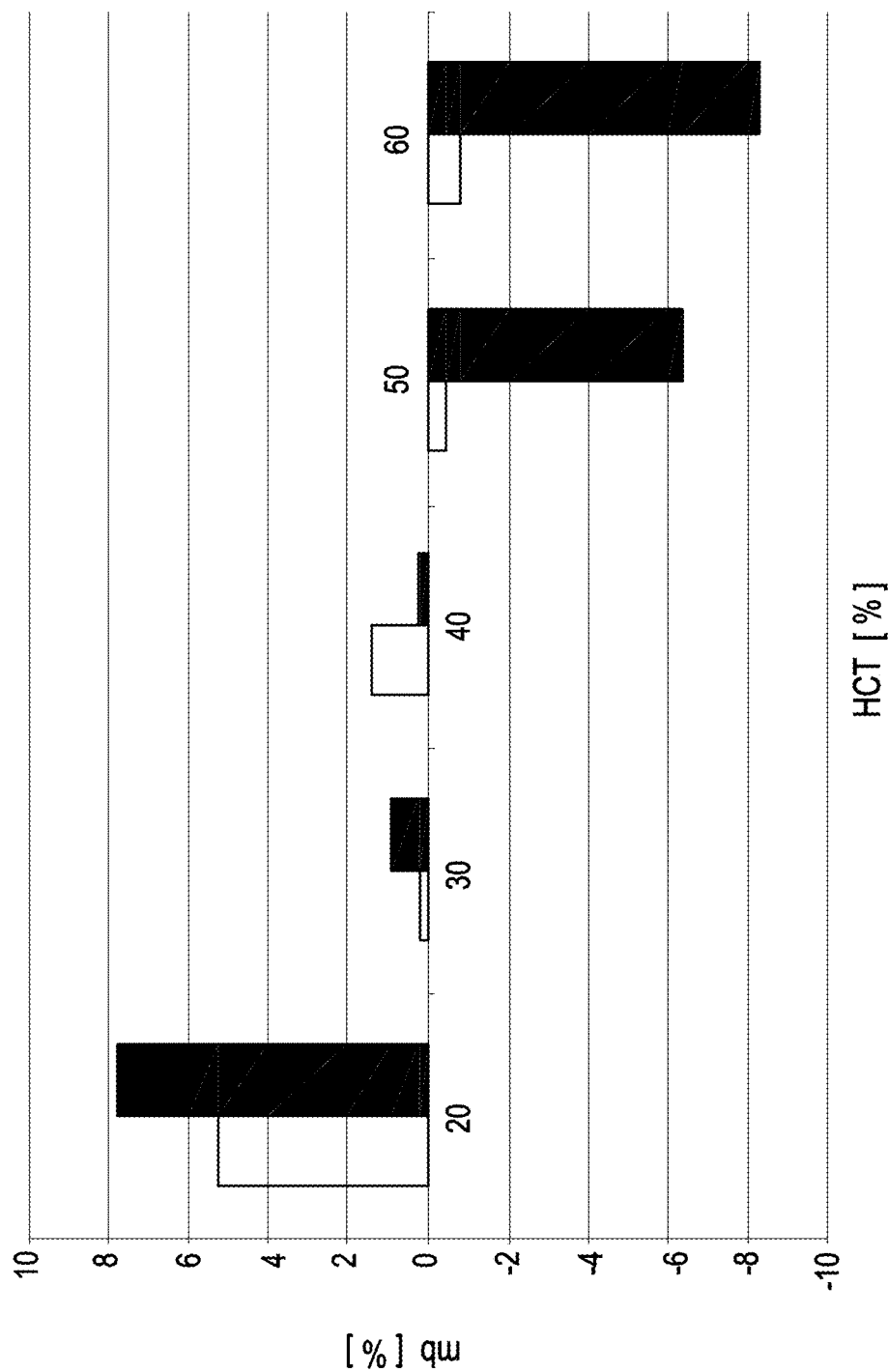
FIG. 11 is a chart showing the mean deviation of the determined glucose concentration from the actual glucose concentration (mean bias, mb, vertical axis) in samples having various hematocrit (HCT) values (horizontal axis) as determined by a calibration curve (black bars) or as determined by a calibration area as shown in FIG. 10 (white bars)
Figure 12:
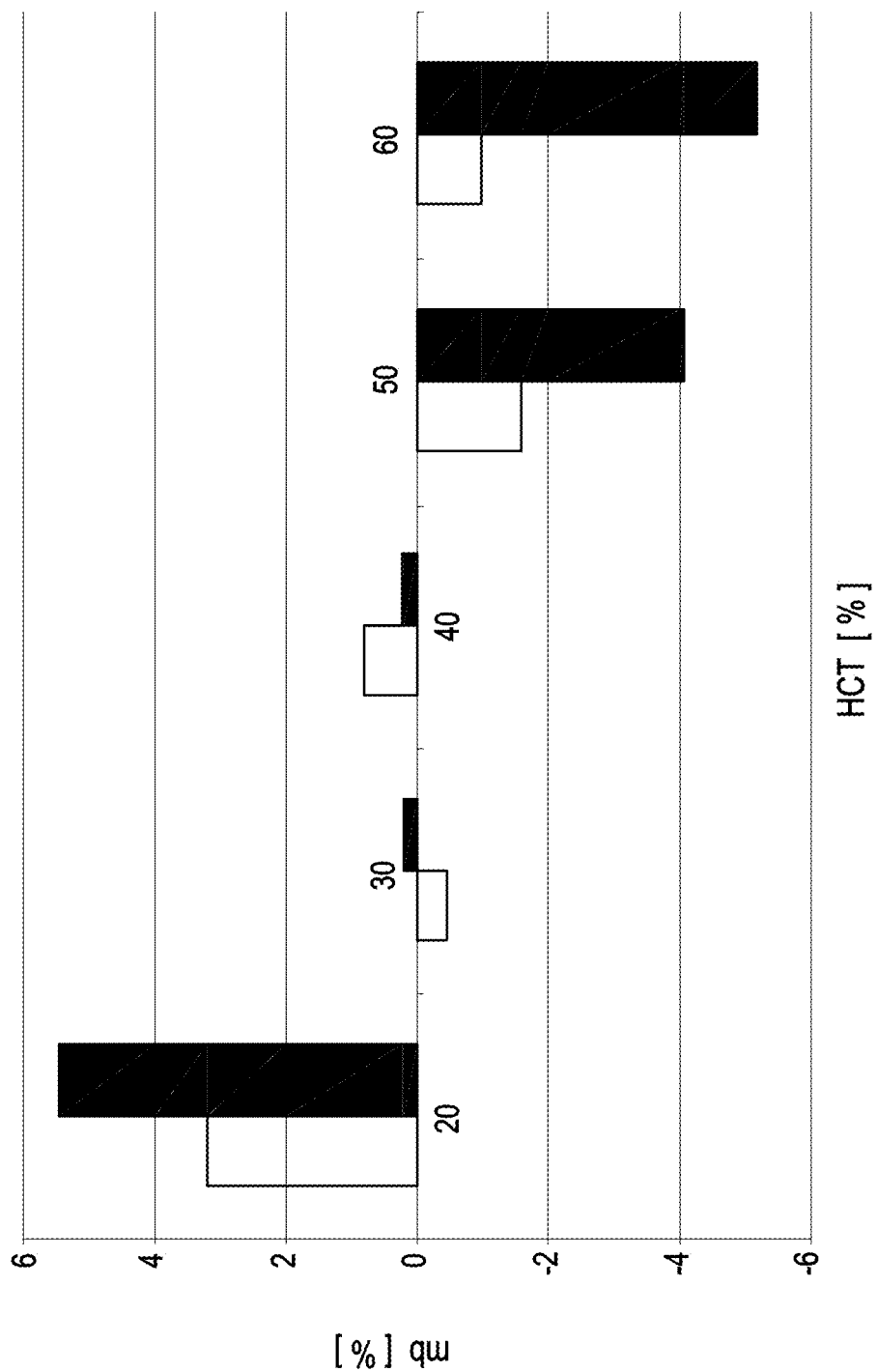
FIG. 12 is a chart showing the mean deviation of the determined glucose concentration from the actual glucose concentration (mean bias, mb, vertical axis) in samples having various hematocrit values (HCT, horizontal axis) as determined by a calibration curve (black bars) or as determined by a calibration area as shown in FIG. 10 (white bars)
Figure 13:
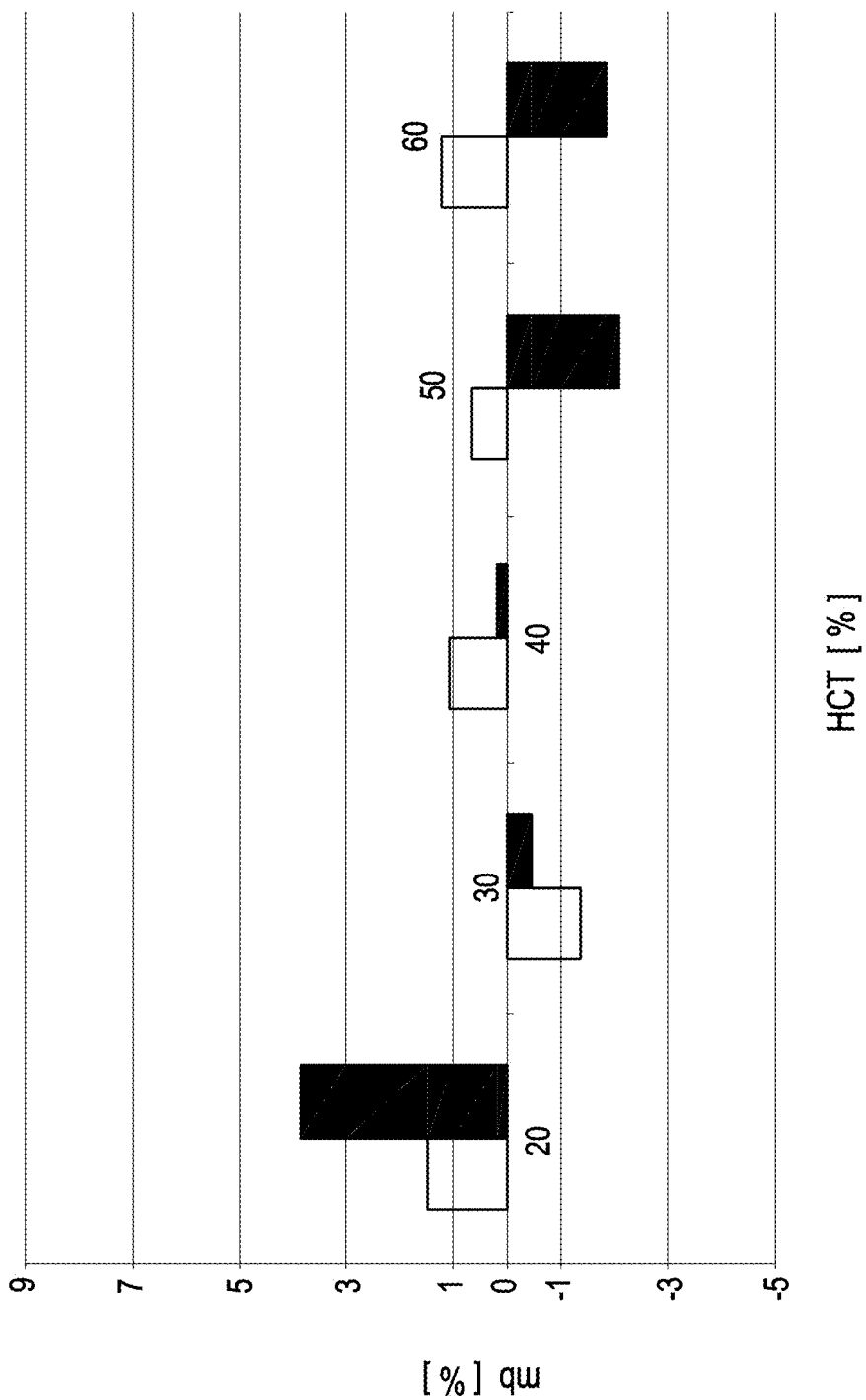
FIG. 13 is a chart showing mean deviation of the determined glucose concentration from the actual glucose concentration (mean bias, mb, vertical axis) in samples having various hematocrit values (HCT, horizontal axis) as determined by a calibration curve (black bars) or as determined by a calibration area as shown in FIG. 10 (white bars)
Figure 14:
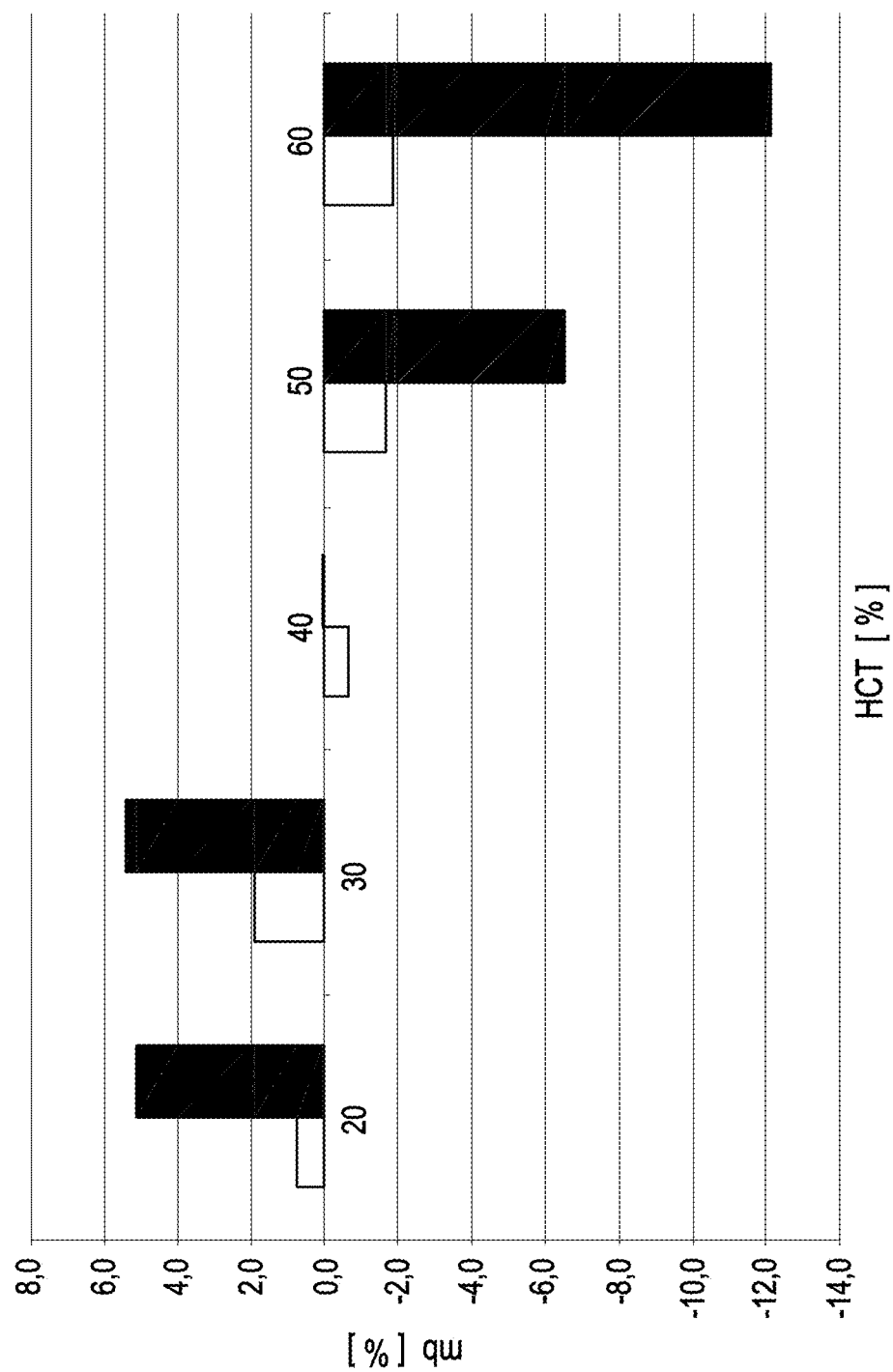
FIG. 14 is a chart showing the mean deviation of the determined glucose concentration from the actual glucose concentration (mean bias, mb, vertical axis) in samples having various hematocrit values (HCT, horizontal axis) as determined by a calibration curve (black bars) or as determined by a calibration area as shown in FIG. 9 (white bars)
Figure 15:
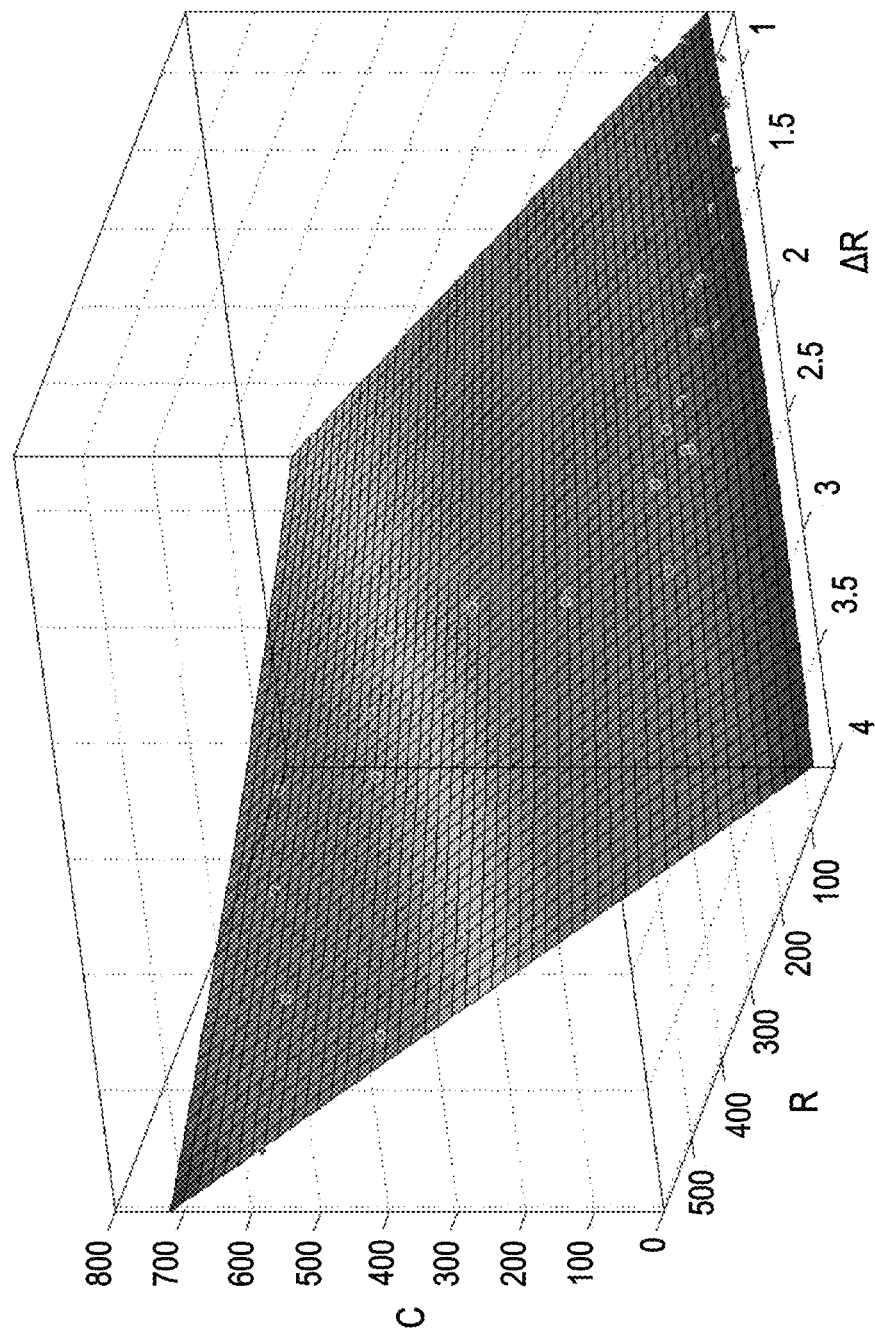
FIG. 15 is a 3-D graph showing dependence of the actual glucose concentration (c) in a blood sample on the remission measured at measurement location subwindow 2 (R) and the difference between the two measurement locations subwindow 9 and subwindow 2 ($\Delta R$) using cNAD chemistry.

Measurements represented in FIGS. 6-9, 11-13, and 15 were performed using the cNAD-chemistry; measurements represented in FIGS. 10 and 14 were performed using the SCV chemistry.

The features disclosed in the above description, the claims and the drawings may be important both individually and in any combination with one another for implementing the invention in its various embodiments.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A method for detecting an analyte in a body fluid, the method having the following steps:
    a) applying a sample of the body fluid containing the analyte to a test element, said test element comprising at least
        (i) a test field comprising a test material, said test material having at least one measurable property which is changed in the presence of the analyte in the sample, said test material comprising at least one enzyme adapted for performing at least one enzymatic reaction on the analyte causing the change of the at least one measurable property of said test material in the presence of the analyte,
        (ii) a capillary element comprising at least one test material at a first measurement location and at least another test material at a second measurement location where the sample is guided to flow in a direction over both of these measurement locations, and
        (iii) a first measurement location and a second measurement location within said test field both containing the test material, wherein the second measurement location is offset from the first measurement location in the flow direction;
    b) contacting the sample with the test material at the first measurement location, the analyte providing a first change of the at least one measurable property of the test material at the first measurement location;
    c) measuring the measurable property of said test material in said first measurement location, thereby generating a first measurement value;
    d) contacting the sample with the test material at the second measurement location, the analyte providing a second change of the at least one measurable property of the test material at the second measurement location;

e) measuring the measurable property of said test material in said second measurement location, thereby generating a second measurement value; and
f) detecting the analyte by using an evaluation algorithm having at least two input variables, wherein
  (i) at least one first input variable of the at least two input variables includes an information on a difference between the first measurement value and the second measurement value, and
  (ii) at least one second input variable of the at least two input variables includes a measurement information on an analyte-induced change of the measurable property of the test material in at least part of the capillary element.

2. The method according to claim 1, wherein said first measurement location is offset upstream of said second measurement location, the measurement information on an analyte-induced change of the measurable property of the test material in at least part of the capillary element is generated by using the first measurement value as the measurement information.

3. The method according to claim 1, wherein the measurement information used in step f) (ii) is a measurement value generated at a measurement location located within the first half of the flow direction of the capillary element.

4. The method according to claim 1, wherein method steps c) and e) are performed at a predetermined time span after application of the sample of the body fluid to the test element.

5. The method according to claim 1, wherein the evaluation algorithm comprises a one-step evaluation algorithm, and the first input variable and the second input variable are simultaneously used for deriving the concentration of the analyte in the body fluid by using at least one predetermined calibration curve, the predetermined calibration curve indicating the concentration of the analyte as a function of the two input variables.

6. The method according to claim 1, wherein the evaluation algorithm comprises at least two separate steps, wherein in a first step of the evaluation algorithm, an estimate value of the concentration is derived from the second input variable by using at least one predetermined first calibration curve, the predetermined first calibration curve indicating an uncorrected concentration of the analyte as a function of the second input variable, and wherein in a second step of the algorithm, the estimate value of the concentration is corrected by applying at least one correction algorithm to the estimate value, the correction algorithm providing a correction to the estimate value by using the first input variable.

7. The method according to claim 6, wherein the sample of the body fluid is blood, in the first step of the algorithm, an estimate value of a glucose concentration is generated, and in the second step of the algorithm, a correction of the estimate value for an actual hematocrit of the blood is provided, thereby generating an information on the glucose concentration in the blood without determining the actual hematocrit of the blood.

8. The method according to claim 1, wherein the first measurement location is offset upstream in the flow direction of the second measurement location, the measurement information on an analyte-induced change of the measurable property of the test material in at least part of the capillary element is generated by using the second measurement value as the measurement information.

9. The method according to claim 1, wherein the measurement information on an analyte-induced change of the measurable property of the test material in at least part of the capillary element is generated by using an average value of the first measurement value and the second measurement value as the measurement information.

10. The method according to claim 1 wherein the measurement information on an analyte-induced change of the measurable property of the test material in at least part of the capillary element is generated by measuring an analyte-induced change of the measurable property in at least a third measurement location of the capillary element, thereby generating at least a third measurement value wherein the third measurement value is used as the measurement information.

11. The method according to claim 10 in which the first, second and third measurement locations include the same test material.

12. The method according to claim 1, wherein method steps c) and e) are performed at a point in time at which the slope of a measurement curve indicating the measurable property as a function of time is below or above a predetermined threshold.

13. The method of claim 12 and which further includes, following step a) and prior to steps c) and e), determining the measurable property as a function of time.

14. The method of claim 1 including correcting the analyte detection based on the presence of particulate matter in the sample.

15. The method of claim 1 in which in step a)(i) the at least one enzyme in the test material performs an optically or electrochemically detectable detection reaction at the first measurement location and at the second measurement location, step c) comprising measuring the measurable property at the first measurement location, and step e comprising measuring the measurable property at the second measurement location.

16. The method of claim 1 in which steps b) and c) occur after step a).

17. A method for detecting an analyte in a body fluid, the method having the following steps:
a) applying a sample of the body fluid containing the analyte to a test element, said test element comprising at least
  (i) a test field comprising a continuous test material, said test material having at least one measurable property which is changed in the presence of the analyte in the sample, said test material comprising at least one enzyme adapted for performing at least one enzymatic reaction on the analyte causing the change of the at least one measurable property of said test material in the presence of the analyte,
  (ii) a capillary element adapted to guide the sample across said test field in a flow direction, and
  (iii) a first measurement location and a second measurement location within the continuous test material, wherein the second measurement location is offset from the first measurement location in the flow direction;
b) contacting the sample with the test material at the first measurement location, the analyte providing a first change of the at least one measurable property of the test material at the first measurement location;
c) measuring the measurable property of said test material in said first measurement location, thereby generating a first measurement value;
d) contacting the sample with the test material at the second measurement location, the analyte providing a second change of the at least one measurable property of the test material at the second measurement location;
e) measuring the measurable property of said test material in said second measurement location, thereby generating a second measurement value; and
f) detecting the analyte by using an evaluation algorithm having at least two input variables, wherein
   (i) at least one first input variable of the at least two input variables includes an information on a difference between the first measurement value and the second measurement value, and
   (ii) at least one second input variable of the at least two input variables includes a measurement information on an analyte-induced change of the measurable property of the test material in at least part of the test field.

18. The method according to claim 17, wherein said first measurement location is offset upstream of said second measurement location, the measurement information on an analyte-induced change of the measurable property of the test material in at least part of the test field is generated by using the first measurement value as the measurement information.

19. The method according to claim 17, wherein the measurement information on an analyte-induced change of the measurable property of the test material in at least part of the capillary element is generated by using an average value of the first measurement value and the second measurement value as the measurement information.

20. The method according to claim 17 wherein the measurement information on an analyte-induced change of the measurable property of the test material in at least part of the test field is generated by measuring an analyte-induced change of the measurable property in at least a third measurement location of the test field, thereby generating at least a third measurement value wherein the third measurement value is used as the measurement information.

21. The method of claim 17 including correcting the analyte detection based on the presence of particulate matter in the sample.

22. The method of claim 17 in which in step a)(i) the at least one enzyme in the test material performs an optically or electrochemically detectable detection reaction at the first measurement location and at the second measurement location, step c) comprising measuring the measurable property at the first measurement location, and step e) comprising measuring the measurable property at the second measurement location.

* * * * *